US012617566B2

(12) United States Patent
Hoffman et al.

(10) Patent No.: US 12,617,566 B2
(45) Date of Patent: May 5, 2026

(54) LITERATURE PACKAGING SYSTEM FOR A HIGH-VOLUME PHARMACY

(71) Applicant: Express Scripts Strategic Development, Inc., St. Louis, MO (US)

(72) Inventors: Robert E. Hoffman, Linden, IN (US); Daniel Riippa, Battle Creek, MI (US); Micah Baggett, Bridgman, MI (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 0 days.

(21) Appl. No.: 18/772,479

(22) Filed: Jul. 15, 2024

(65) Prior Publication Data

US 2025/0019101 A1     Jan. 16, 2025

Related U.S. Application Data

(60) Provisional application No. 63/526,565, filed on Jul. 13, 2023.

(51) Int. Cl.
B65B 5/04          (2006.01)
B65B 25/14         (2006.01)
(Continued)

(52) U.S. Cl.
CPC .............. B65B 5/045 (2013.01); B65B 25/14 (2013.01); B65B 35/16 (2013.01); B65B 35/58 (2013.01); G16H 20/13 (2018.01)

(58) Field of Classification Search
None
See application file for complete search history.

(56) References Cited

U.S. PATENT DOCUMENTS 1,071,853 A * 9/1913 Young ..................... B65B 61/06
                                                  53/120
2,030,880 A * 2/1936 Kleineberg ........... B65B 25/145
                                                  53/586
(Continued)

FOREIGN PATENT DOCUMENTS

ES        2326760 A1 * 10/2009    ............. B65H 45/06
JP        2510703 B2    5/1990
(Continued)

OTHER PUBLICATIONS

Elbrechter, Christof, Robert Haschke, and Helge Ritter. "Folding paper with anthropomorphic robot hands using real-time physics-based modeling." 2012 12th IEEE-RAS International Conference on Humanoid Robots (Humanoids 2012). IEEE, 2012.
(Continued)

*Primary Examiner* — Tanzim Imam
(74) *Attorney, Agent, or Firm* — Dickinson Wright PLLC

(57) ABSTRACT

A medication packaging system can include a tray with a slot and a literature receiving area to hold literature in a position above the slot, and a robotic arm with a literature grabbing mechanism that can have a plurality of fingers that extend parallel to one another. The plurality of fingers including a central finger and a pair of outer fingers that are located on opposite sides of the central finger which are relatively movable between a disengaged position on one side of the slot of the tray to an engaged position at least partially on the other side of the slot to engage and fold the literature in the literature receiving area of the tray. The robotic arm can move the literature and place it in a shipping bag or container.

20 Claims, 20 Drawing Sheets

(51) Int. Cl.
    *B65B 35/16*       (2006.01)
    *B65B 35/58*       (2006.01)
    *G16H 20/13*       (2018.01)

(56)                References Cited

U.S. PATENT DOCUMENTS

| | | | | |
|---|---|---|---|---|
| 3,417,987 | A | * | 12/1968 | Hannon ................ B65B 25/145 |
| | | | | 270/45 |
| 3,919,827 | A | * | 11/1975 | Larson ................. B65B 25/145 |
| | | | | 53/473 |
| 7,168,748 | B2 | | 1/2007 | Townsend |
| 7,273,371 | B2 | | 9/2007 | Massad |
| 7,409,812 | B2 | | 8/2008 | Gilmore |
| 8,418,341 | B1 | | 4/2013 | Fisher |
| 8,702,163 | B2 | | 4/2014 | Westerink |
| 8,960,788 | B2 | | 2/2015 | Chuah |
| 9,590,368 | B2 | | 3/2017 | Wyckoff |
| 9,827,677 | B1 | | 11/2017 | Gilbertson |
| 9,827,678 | B1 | | 11/2017 | Gilbertson |
| 10,195,746 | B2 | | 2/2019 | Truebenbach |
| 10,934,046 | B2 | | 3/2021 | Sha |

| | | | | |
|---|---|---|---|---|
| 2004/0238463 | A1 | | 12/2004 | Taylor |
| 2005/0269769 | A1 | | 12/2005 | Naghi |
| 2007/0275345 | A1 | | 11/2007 | Massad |
| 2008/0112781 | A1 | | 5/2008 | Schrafel |
| 2009/0101529 | A1 | | 4/2009 | Gelardi |
| 2017/0282634 | A1 | * | 10/2017 | Jones ....................... B65H 5/08 |
| 2018/0150730 | A1 | | 5/2018 | Hoffman |
| 2018/0276933 | A1 | | 9/2018 | Nakanishi |

FOREIGN PATENT DOCUMENTS

| | | | | |
|---|---|---|---|---|
| JP | 2020131403 | A | | 8/2020 |
| KR | 20180009871 | A | * | 1/2018 ............. B65H 5/021 |
| WO | 2014125627 | A1 | | 8/2014 |

OTHER PUBLICATIONS

Thai, Phuong Thao, et al. "Simulation-based approach for paper folding with the aim to design the origami-performing robotic system." Mechanical Engineering Journal 3.6 (2016): 15-00668.

YuMi® IRB 14000, ABB, Mar. 3, 2021.

* cited by examiner

Figure 2:
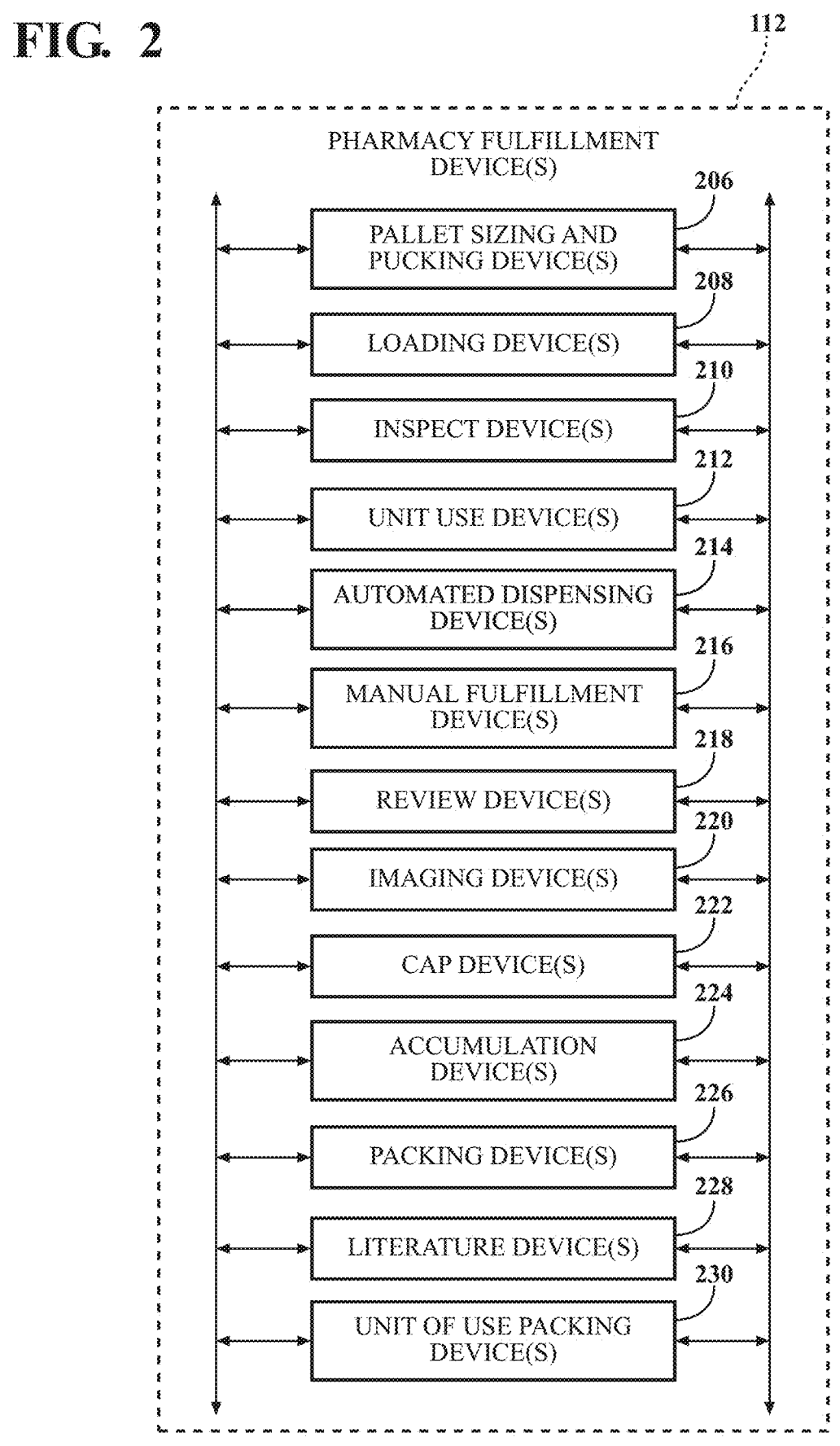

PHARMACY FULFILLMENT DEVICE(S)

206
PALLET SIZING AND PUCKING DEVICE(S)

208
LOADING DEVICE(S)

210
INSPECT DEVICE(S)

212
UNIT USE DEVICE(S)

214
AUTOMATED DISPENSING DEVICE(S)

216
MANUAL FULFILLMENT DEVICE(S)

218
REVIEW DEVICE(S)

220
IMAGING DEVICE(S)

222
CAP DEVICE(S)

224
ACCUMULATION DEVICE(S)

226
PACKING DEVICE(S)

228
LITERATURE DEVICE(S)

230
UNIT OF USE PACKING DEVICE(S)

FIG. 20

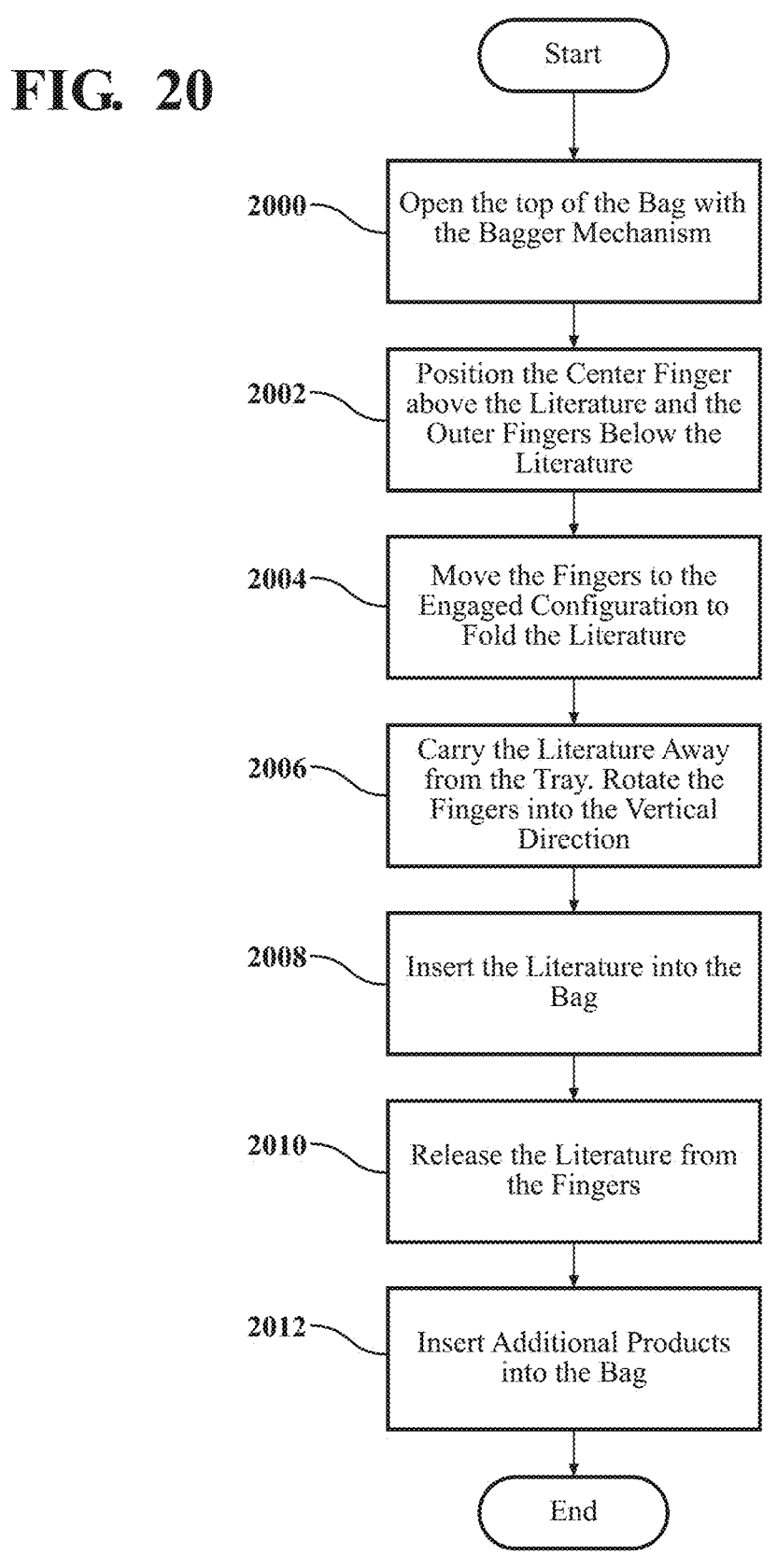

Start

2000 — Open the top of the Bag with the Bagger Mechanism

2002 — Position the Center Finger above the Literature and the Outer Fingers Below the Literature 2004 — Move the Fingers to the Engaged Configuration to Fold the Literature 2006 — Carry the Literature Away from the Tray. Rotate the Fingers into the Vertical Direction 2008 — Insert the Literature into the Bag 2010 — Release the Literature from the Fingers 2012 — Insert Additional Products into the Bag End

LITERATURE PACKAGING SYSTEM FOR A HIGH-VOLUME PHARMACY

CROSS-REFERENCE TO RELATED APPLICATION

This application claims priority to and the benefit of U.S. Provisional Application No. 63/526,565, filed on Jul. 13, 2023, and entitled "LITERATURE PACKAGING SYSTEM FOR A HIGH-VOLUME PHARMACY," the entire contents of which is herein incorporated by reference.

FIELD

The present disclosure relates generally to the technical field of automated filling centers. In a specific example, the present disclosure can relate to a high-volume fulfillment center (e.g., a high-volume pharmacy, etc.) and to systems and methods for handling packaging medications and documentations associated with the medications.

BACKGROUND

The background description provided here is for the purpose of generally presenting the context of the disclosure. Work of the presently named inventors, to the extent it is described in this background section, as well as aspects of the description that cannot otherwise qualify as prior art at the time of filing, are neither expressly nor impliedly admitted as prior art against the present disclosure.

An automated pharmacy can process and fill a large number of prescriptions and prescription orders. Automated systems can be used by a high-volume pharmacy to process and fulfill prescriptions.

Mail order pharmacies provide a convenient and cost-effective option for patients to receive prescription drugs. For example, a mail order pharmacy can be capable of taking advantage of economies of scale, volume dispensing of prescription drugs, and centralized warehousing and shipping to reduce the cost of prescription drugs purchased by patients of the mail order pharmacy.

BRIEF DESCRIPTION OF THE DRAWINGS

The present disclosure will become more fully understood from the detailed description and the accompanying drawings.

FIG. 2 is a block diagram of a pharmacy fulfillment device of the high-volume pharmacy system of FIG. 1;

FIG. 20 is a flow chart of the steps of filling a medication package according to one embodiment of the present disclosure.

In the drawings, reference numbers can be reused to identify similar and/or identical elements.

DETAILED DESCRIPTION

The present disclosure is related to a packaging system for a high-volume pharmacy. The packaging system includes a robotic arm with a literature grabbing mechanism that includes a plurality of fingers which extend in parallel with one another in a first direction. One of the fingers is a central finger and two of the fingers are outer fingers. In operation, the central finger is placed above a plurality of sheets of literature and the outer fingers are placed below the sheets of literature. The central finger is then moved downwardly in a second direction that is perpendicular to the first direction towards the outer fingers to fold the sheets of literature around the central finger. The robotic arm then brings the folded literature to a bagger mechanism, which has opened a top of a bag, and inserts the literature into the bag. The robotic arm urges the literature down into the bag to further open the bag prior to releasing the literature. When the robotic arm releases the literature, the literature, being non-creased, hold an interior of the bag open to make it easier to insert a medication package and any other materials into the bag prior to shipping the bag to a customer.

Figure 1:
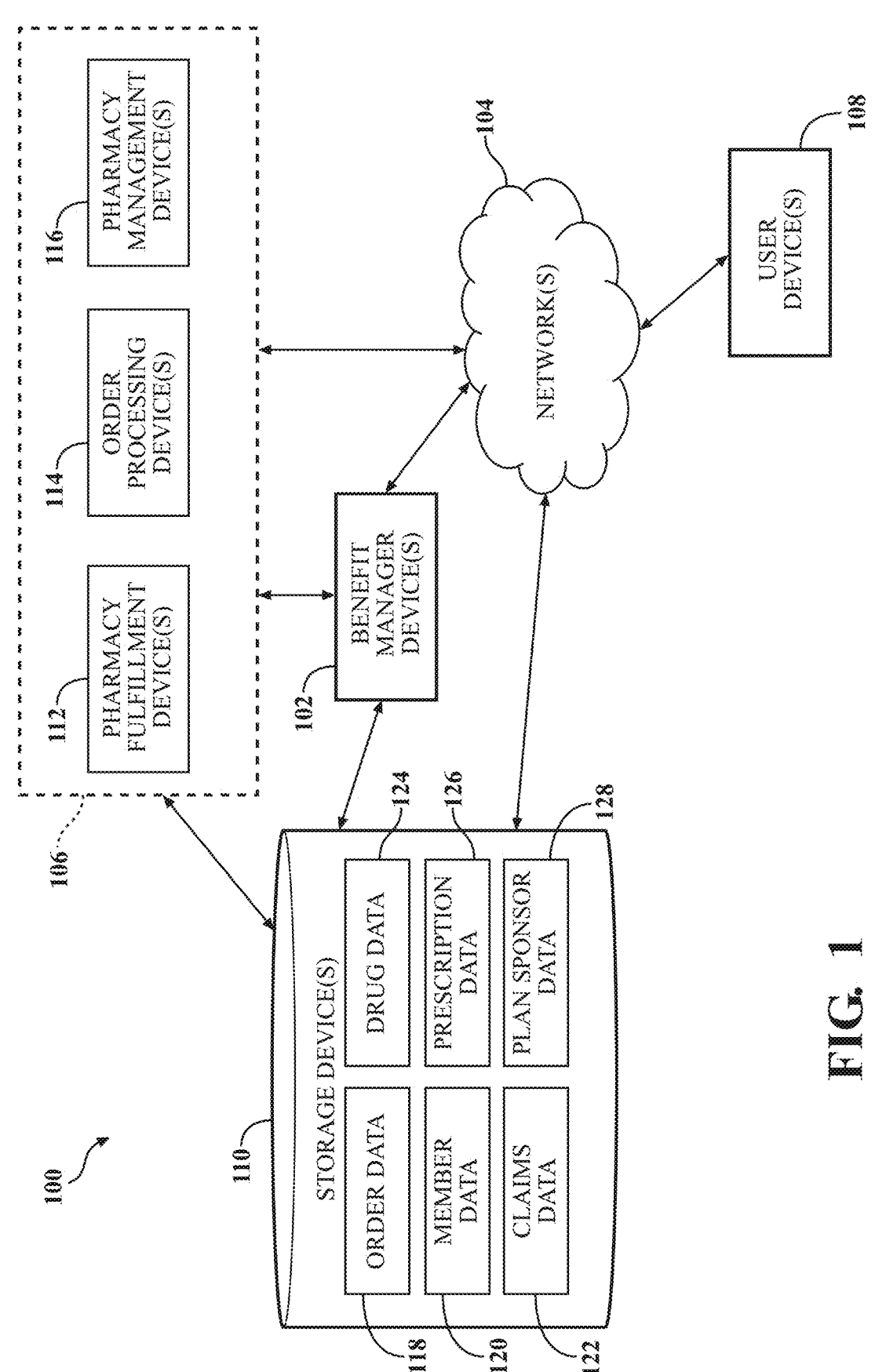
FIG. 1 is a block diagram view of a high-volume pharmacy system.

FIG. 1 is a block diagram of an example implementation of a system 100, according to an example embodiment. While the system 100 is generally described as being deployed in a high-volume pharmacy or fulfillment center (e.g., a mail order pharmacy, a direct delivery pharmacy, an automated pharmacy, multiple package delivering center, and the like), the system 100 and/or components thereof may otherwise be deployed (e.g., in a lower volume pharmacy). A high-volume pharmacy may be a pharmacy that is capable of filling prescriptions automatically, mechanically, manually, or a combination thereof. The system 100 may include a benefit manager device 102, a pharmacy device 106, and a user device 108, which may communicate with each other directly and/or over a network 104. The system may also include a storage device 110.

The benefit manager 102 is a device operated by an entity that is at least partially responsible for creation and/or management of the pharmacy or drug benefit. While such an entity operating the benefit manager device 102 is typically a pharmacy benefit manager (PBM), other entities may operate the benefit manager device 102 either on behalf of themselves, the PBM, another entity, or other entities. For example, the benefit manager device 102 may be operated by a health plan, a retail pharmacy chain, a drug wholesaler, a data analytics or other type of software-related company, or the like. In some embodiments, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, and the like. The PBM may, in addition to its PBM operations, operate one or more than one pharmacy. The pharmaceutical vending machines or kiosks, and the like.

Some of the operations of the PBM that operates the benefit manager device 102 may include the following activities and processes. A member (or a person on behalf of the member) of a pharmacy benefit plan administered by or through the PBM attempts to obtain a prescription drug at a retail pharmacy location (e.g., a location of a physical store) from a pharmacist or a pharmacist technician. The member may also attempt to obtain the prescription drug through mail order drug delivery from a mail order pharmacy location, which may be the high-volume pharmacy system 100. In some embodiments, the member may also attempt to obtain the prescription drug directly or indirectly through the use of a machine, such as a kiosk, vending unit, mobile electronic device, or a different type of mechanical electrical, electronic communication device, and/or computing device. Such a machine may be filled with the prescription drug in prescription packaging, which may include multiple prescription components, by the high-volume pharmacy system 100.

The member may have a copayment for the prescription drug that reflects an amount of money that the member is responsible to pay the pharmacy for the prescription drug. The money paid by the member to the pharmacy may come from personal funds of the member, a health savings account (HAS) of the member or the member's family, a health reimbursement arrangement (HRA) of the member or the member's family, a flexible spending account (FSA) of the member or the member's family, or the like. In some instances, an employer of the member may directly or indirectly fund or reimburse the member for the copayments.

The amount of the co-pay required form the member may vary with different pharmacy benefit plans having different plan sponsors or clients and/or prescription drugs. The member's copayment may be based on a flat copayment (e.g., $10), coinsurance (e.g., 10%), and/or a deductible (e.g., for first $500 of annual prescription drug expenses) for certain prescription drugs, certain types and/or classes of prescription drugs, and/or all prescription drugs. The copayment may be stored in the storage 110 or determined by the benefit manager device 102.

In some instances, the member may not pay the copayment or may only pay a portion of the copayment for the prescription drug. For example, if the usual and customary cost for a generic version of a prescription drug is $4, and the member's flat copayment is $20 for the prescription drug, the member may only be required to pay $4 to receive the prescription drug. In another example involving a worker's compensation claim. No copayment may be due by the member for the prescription drug.

In addition, copayments may also vary based on different delivery channels used for the prescription drug to be received by the member. For example, the copayment for receiving the prescription drug from a mail order pharmacy location may be less than the copayment for receiving the prescription drug from a retail pharmacy location.

In conjunction with receiving the copayment (if any) from the member and dispensing the prescription drug to the member, the pharmacy submits a claim to the PBM for the prescription drug. After receiving the PBM (e.g., through the benefit manager device 102) may perform certain adjudication operations including verifying eligibility of the member, identifying and/or reviewing an applicable formulary for the member to determine any appropriate copayment, coinsurance, and deductible for the prescription drug, and performing a drug utilization review (DUR) on the member. The PBM provides a response to the pharmacy (e.g., from the benefit manager device 102 to the pharmacy device 106) following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However, in some instances these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on the type(s) of pharmacy network in which the pharmacy is included. Other factors may also be used to determine the amount in addition to the type of pharmacy network. For example, if the member pays the pharmacy for the prescription drug without the prescription drug benefit provided by the PBM (e.g., by paying cash without use of the prescription drug benefit or by use of a so-called pharmacy discount card offering other negotiated rates), the amount of money paid by the member may be different than when the member uses prescription or drug benefit. In some embodiments, the amount of money received by the pharmacy for dispensing the prescription drug and for the prescription drug itself may be higher than when the member uses the prescription or drug benefit. Some or all of the foregoing operations may be performed by executing instructions stored on the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a Wi-Fi network, or an IEEE 802.11 standards network, as well as various combinations thereof. The network 104 may include an optical network. The network 104 may be a local area network or a global communication network, such as the Internet. In some embodiments, the network 104 may include a network dedicated to prescription orders, e.g., a prescribing network such as the electronic prescribing network operated by Surescripts of Arlington, Virginia.

Moreover, although the system shows a single network 104, multiple networks can be used. The multiple networks may communicate in series with each other to link the devices 102, 106-110 or in parallel to link the devices 102, 106-110.

The pharmacy device 106 may include an order processing device 114, a pharmacy manager device 116, and a pharmacy fulfillment device 112 in communication with each other directly and/or over the network 104.

The order processing device 114 may receive information regarding filling prescriptions and may direct an order component to one or more than one of the devices of the pharmacy fulfillment device 112 at a pharmacy. The pharmacy fulfillment device 112 may fulfill, dispense, aggregate, and/or pack the order components of the prescription drugs in accordance with one or more than one of the prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfilment device 112. In some embodiments, the order processing device 114 may be an external device separate from the pharmacy and communicate with other devices located within the pharmacy.

For example, the external order processing device 114 may communicate with an internal order processing device 114 and/or other devices located within the system 100. In some embodiments, the external order processing device 114 may have limited functionality (e.g., as operated by a patient requesting fulfillment of a prescription drug), while the internal pharmacy order processing device 114 may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions may include what device(s) in the pharmacy are responsible for filling or otherwise handling certain portions of the prescription order. The order consolidation decisions include whether portions of one prescription order or multiple prescription orders should be shipped together for a patient or a patient family. The order processing device 114 may also track and/or schedule literature or paperwork associated with each prescription order or multiple prescription orders that are being shipped together.

The pharmacy management device 116 may enable and/or facilitate management and operations in a pharmacy. For example, the pharmacy management device 116 may provide functionality to enable receipt and processing of prescription drug claims, management of pharmacy personnel, management of pharmaceutical and non-pharmaceutical products, track products in the pharmacy, record workplace incidents involve personnel and products, and the like. In some embodiments, the order processing device 114 may operate in combination with the pharmacy management device 116.

In some embodiments, the pharmacy management device 116 may be a device associated with a retail pharmacy location (e.g., exclusive pharmacy location, a grocery store with a retail pharmacy, or a general sales store with a retail pharmacy) or other type of pharmacy location at which a member attempts to obtain a prescription. The pharmacy management device 116 may be utilized by the pharmacy to submit the claim to the PBM (e.g., through the benefit management device 102) for adjudication.

In some embodiments, the pharmacy management device 116 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some embodiments, the benefit manager 102 may track prescription drug fulfillment and/or other information for patients that are not members or have not identified themselves as members, at the time (or in conjunction with the time) in which they seek to have a prescription filled at a pharmacy.

The pharmacy fulfillment devices 112, the order processing device, and/or the pharmacy management device 116 may include circuitry, a processor, a memory to store data and instructions, and an electronic communication device to provide a communication functionality. These devices 112-116, in some embodiments are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116 may include circuitry, a processor, a memory to store data and instructions, and communication functionality. These devices 112-116, in some embodiments, are dedicated to performing processes, methods and/or instructions described herein. Other types of electronic devices specifically configured to implement with the processes, methods and/or instructions described herein may also be used.

In some embodiments, at least some functionality of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage) and/or through the network 104 (e.g., by utilizing a cloud configuration or software as a service, etc.) with the storage 110.

The user device 108 is used by a device operator. The device operator may be a user (e.g., an employee, a contractor, a benefit member, a patient of the pharmacy, or the like) associated with the system 100. Other device operators may also operate the user device 108. In some embodiments, the user device 108 may enable the device operator to attend to pharmacy operations in a convenient manner (e.g., remote from a pharmacy). In some embodiments, the user device 108 may enable the device operator to receive information about pharmacy processes, prescription drug fulfillment status, and the like. In an example, the cleaner assembly may be a type of user device 108. In some embodiments, the pharmacy management device 116 may access certain cleaning data and download cleaning instructions to the cleaning assembly. The cleaning instructions can tell the cleaning device how it should operate, when it should operate and where it should operate as described herein.

The user device 108 may be a stand-alone device that solely provides at least some of the functionality of the methods and systems, or may be a multi-use device that has functionality outside off analysis of the methods and systems. Examples of the user device 108 may include a mobile electronic device, such as an iPhone or iPad by Apple, Inc., and mobile electronic devices powered by Android by Google, Inc. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, and the like) in communication with the benefit manager device 102, the pharmacy device 106, and/or the user device 108 directly and/or over the network 104. The non-transitory storage may store order data 118, member 120, claims data 122, drug data 124, prescription data 126, and/or plan sponsor 128. Further, the system 100 may include additional devices, which may communicate with each other directly or over the network 104.

The order data 118 may be related to a prescription order. The order data may include the type of the prescription drug (e.g., drug name and strength) and quantity of the prescription drug. The order data 118 may also include data used for completion of the prescription, such as prescription materials and/or the type and/or size of container in which the drug is dispensed or in which is requested to be dispensed. In general, prescription materials include an electronic copy of information regarding the prescription drug for inclusion with or otherwise provided (e.g., via email) in conjunction with the fulfilled prescription. The prescription materials may include electronic information regarding drug interaction warnings, recommended usage possible side effects, expiration date, date of prescribing, or the like. The order data 118 may be used by the pharmacy to fulfill a pharmacy order.

In some embodiments, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription bottle and sealing lid, prescription packaging, and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information, such as bar code data read from pallets, bins, trays, carts, and the like used to facilitate transportation of prescriptions within the pharmacy may also be stored as order data 118.

The member data 120 includes information regarding the members associated with the PBM. The information stored as member data 120 may include personal information, personal health information, protected health information, fitness data, health data, web and mobile app activity, and the like. Examples of the member data 120 include name, address, telephone number, e-mail address, prescription drug history, and the like. The member data 120 may include a plan sponsor identifier that identifies the plan sponsor associated with the member and/or a member identifier that identifies the member to the plan sponsor. The member data 120 may also include, by way of example, dispensation preferences such as type of label, type of cap, message preferences, language preferences, or the like.

The member data 120 may be accessed by various devices in the pharmacy to obtain information utilized for fulfillment and shipping of prescription orders. In some embodiments, an external order processing device 114 operated by or on behalf of a member may have access to at least a portion of the member data 120 for review, verification, or other purposes.

In some embodiments, the member data 120 may include information for persons who are patients of the pharmacy but are not members in a pharmacy benefit plan being provided by the PBM. For example, these patients may obtain drugs directly from the pharmacy, through a private label service offered by the pharmacy, or otherwise. In general, the use of the terms member (e.g., of a prescription drug benefit plan) and patient (e.g., of a pharmacy) may be used interchangeably in this disclosure.

The claims data 122 includes information regarding pharmacy claims adjusted by the PBM under a drug benefit program provided by the PBM for one, or more than one, plan sponsor. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number), the dispensing date, generic indicator, GPI number, medication class, the cost of the prescription drug provided under the drug benefit program, the copay/coinsurance amount, rebate information, and/or member eligibility, and the like. Additional information may be included.

In some embodiments, other types of claims beyond prescription drug claims may be stored in the claims data 122. For example, medical claims, dental claims, wellness claims, or other types of health care-related claims for members may be stored as a portion of the claims data.

In some embodiments, the claims data 122 includes claims that identify the members with whom the claims are associated. In some embodiments, the claims data 122 includes claims that have been de-identified (e.g., associated with a unique identifier but not with a particular, identifiable member), aggregated, and/or otherwise processed.

The drug data 124 may include drug name (e.g., technical name and/or common name), other names by which the drug is known by, active ingredients, an image of the drug (e.g., in pill form), and the like. The drug data 124 may include information associated with a single medication or multiple medications.

The prescription data 126 may include information regarding prescriptions that may be issued by prescribers on behalf of patients, who may be members of the pharmacy benefit plan, for example to be filled by a pharmacy. Examples of the prescription data 126 include patient names, medication or treatment (such as lab tests), dosing information, and the like. The prescriptions may be electronic prescriptions, paper prescriptions that have been scanned, or otherwise. In some embodiments, the dosing information reflects a frequency of use (e.g., once a day, twice a day, before each meal, etc.) and a duration of use (e.g., a few days, a week, a few weeks, a month, etc.).

In some embodiments, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, and the like.

The cleaner data 130 may include data instructing the cleaning device when it should clean, what cleaning components it should operate and how it should clean any particular device within the order fulfillment system. For example, a high volume fill device may have a unique number of dispensing devices or a unique number of dispensing towers. The cleaner data 130 may store this information to be downloaded to the cleaner assembly. The cleaner data 130 can also include the setting for the vacuum, i.e., the suction power of the vacuum. The cleaner data 130 can also include instructions for the revolution per minute of the brushes and which brushes should be used at what location in the dispensing system.

FIG. 2 illustrates the pharmacy fulfillment device 112, according to an example embodiment. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device, the order processing device 114, and/or the non-transitory storage 110, directly or over the network 104. Specifically, the pharmacy fulfillment device 112 may include pallet sizing and pucking device(s); loading device(s) 208; inspect device(s) 210, unit of use device(s) 212, automated dispensing device(s) 214, manual fulfillment device(s) 216, review device(s) 218, imaging device(s) 220, cap device(s) 222, accumulation device(s) 224, literature device(s) 228, packing device(s) 226, and unit of use packing device(s) 230. The pharmacy fulfillment device 112 can include a cleaner device 232, as described herein, e.g., cleaner device 920. Further, the pharmacy fulfillment device 112 may include additional devices, which may communicate with each other directly or over the network 104.

In some embodiments, operations performed by one or more of these devices 206-230 may be performed sequentially, or in parallel with the operations of devices as may be coordinated by the order processing device 114. In some embodiments, the order processing device 114 tracks a prescription with the pharmacy based on operations performed by one or more than one of the devices 206-230.

In some embodiments, the pharmacy fulfillment device 112 may transport prescription drug containers, for example, between more than one of the devices 206-230 in a high-volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In one embodiment, the loading device 208 has robotic arms or pickers to grasp a prescription container and move it to and from a pallet or to and from a puck. The loading device may also print a label that is appropriate for a container that is to be loaded onto the pallet and apply the label to the container. The pallet may be located on a conveyor assembly during these operations (e.g., at the high volume fulfillment center or the like).

The inspect device 210 may verify that containers in a pallet are correctly labeled and in the correct spot on the pallet. The inspect device 210 may scan the label on one or more than one container on the pallet. Labels of containers may be scanned or imaged in full or in part by the inspect device 210. Such imaging may occur after the container has been lifted out of its puck by a robotic arm, picker, or the like, or may be otherwise scanned or imaged while retained in the puck. In some embodiments, images and/or video captured by the inspect device may be stored in the storage device as a portion of the order data 118.

The unit of use device 212 may temporarily store, monitor, label, and/or dispense unit of use products. In general, unit of use products are prescription drug products that may be delivered to a patient or member without being repackaged at the pharmacy. These products may include pills in a container, pills in a blister pack, inhalers, liquids in a spray or other dispensing container, and the like. Prescription drug products dispensed by the unit of use device 212 may be packaged individually or collectively for shipping, or may be shipped in combination with other prescription drugs dispensed by other devices (e.g., in the high volume fulfillment center).

At least some of the operations of the devices 206-230 may be directed by the order processing device 114. For example, the manual fulfillment device 216, the review device 218, the automated dispensing device 214, the packing device 226, and/or another device may receive instructions provided by the order processing device.

The automated dispensing device 214 may include one or more than one device that dispenses prescription drugs or pharmaceuticals into prescription containers in accordance with one or multiple prescription orders. In general, the automated dispensing device 214 may include mechanical and electronic components with, in some embodiments, software and/or logic to facilitate pharmaceutical dispensing that would otherwise be performed in a manual fashion by a pharmacist and/or pharmacist technician. For example, the automated dispensing device 214 may include high volume fillers (HVFs) that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some embodiments, the manual fulfillment device 216 provides the filled container to another device in the pharmacy fulfillment devices 112 to be joined with other containers in a prescription order for a patient or member. In general, a manual fulfillment may include operations at least partially performed by a pharmacist or a pharmacy technician.

For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter or the like). Prescription drugs dispensed by the manual fulfillment device 216 may be packaged individually or collectively for shipping or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been cancelled, containers with defects, and the like. In an example embodiment, the manual review may be performed at the manual station.

The imaging device 220 may image containers prior to filling and/or after they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some embodiments, the cap device 222 may secure a prescription container with a type of cap in accordance with a patient preference (e.g., a preference regarding child resistance, a preference regarding built-in adherence functionality, or the like), a plan sponsor preference, a prescriber preference, or the like. The cap device 222 may also etch a message into the cap or otherwise associate a message into the cap, although this process may be performed by a different device in the high-volume fulfillment center.

The accumulation device 224 accumulates various containers of prescription devices in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high-volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany prescription drugs included in a prescription order, relating to prescription drugs in the order, financial information associated with the order (e.g., an invoice or an account statement, or the like). The term "paper" is to be construed in its broadest sense and encompasses, but is not limited to, traditional paper products, laminated sheets, composite materials, and any other type of printable or writable sheet material, irrespective of its composition or method of manufacture.

In some embodiments, the literature device 228 folds or otherwise prepares the literature for inclusion with a prescription drug order (e.g., in a shipping container or the like). In some embodiments, the literature device 228 that prints the literature may be separate from the literature device that prepares the literature for inclusion with a prescription order. The packing device 226 packages a prescription order in preparation for shipping the order. As discussed in further detail below, the packing device 226 may bag the fulfilled prescription order. The packing device 226 may further place inserts, including literature from the literature device 228 into the bag. The packing device 226 may label the bag with an address and a recipient's name. The label may be printed and affixed to the bag, be printed directly onto the bag, or otherwise associated with the bag.

In some embodiments, the packing device 226 may sort the bag for mailing in an efficient manner (e.g., sort by delivery address, sort by zip code, or the like). The packing device 226 may label the bag with an address and a recipient's name. The label may be printed and affixed to the bag, be printed directly onto the bag, or otherwise associated with the bag. The packing device 226 may sort the bag for mailing in an efficient manner (e.g., sort by delivery address, sort by zip code, or the like). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS®, FedEx®, or DHL®, or the like), through delivery service, through a local delivery service (e.g., a courier service), through a locker box at a shipping site (e.g., an Amazon® locker, library locker, a post office box, or the like) or otherwise.

The unit of use packing device 230 packages a unit of use prescription order in preparation for shipping the order. In some embodiments, the unit of use packing device 230 may be the same as the packing device 226.

The pharmacy fulfillment device 112 in FIG. 2 may include single devices 206-230 or multiple devices 206-230 (e.g., depending upon implementation in a pharmacy). The devices 206-230 may be the same type or model of device or may be different device types or models. When multiple devices are present, the multiple devices may be of the same device type or models or may be a different device type or model. The types of devices 206-230 shown in FIG. 2 are example devices. In other configurations of the system 100, lesser, additional, or different types of devices may be included.

Moreover, multiple devices may share processing and/or memory resources. The devices 206-230 may be located in the same area or in different locations. For example, the devices 206-230 may be located in a building or a set of adjoining buildings. The devices 206-230 may be interconnected (e.g., by conveyors), networked, and/or otherwise in contact with one another or integrated with one another (e.g., at the high-volume fulfillment center). In addition, the functionality of a device may be split among a number of discrete devices and/or combined with other devices.

Figure 3:
FIG. 3 is a perspective view of a bagger mechanism for engaging and opening a top of a bag to be filled with a medication product and corresponding literature.
Figure 18:
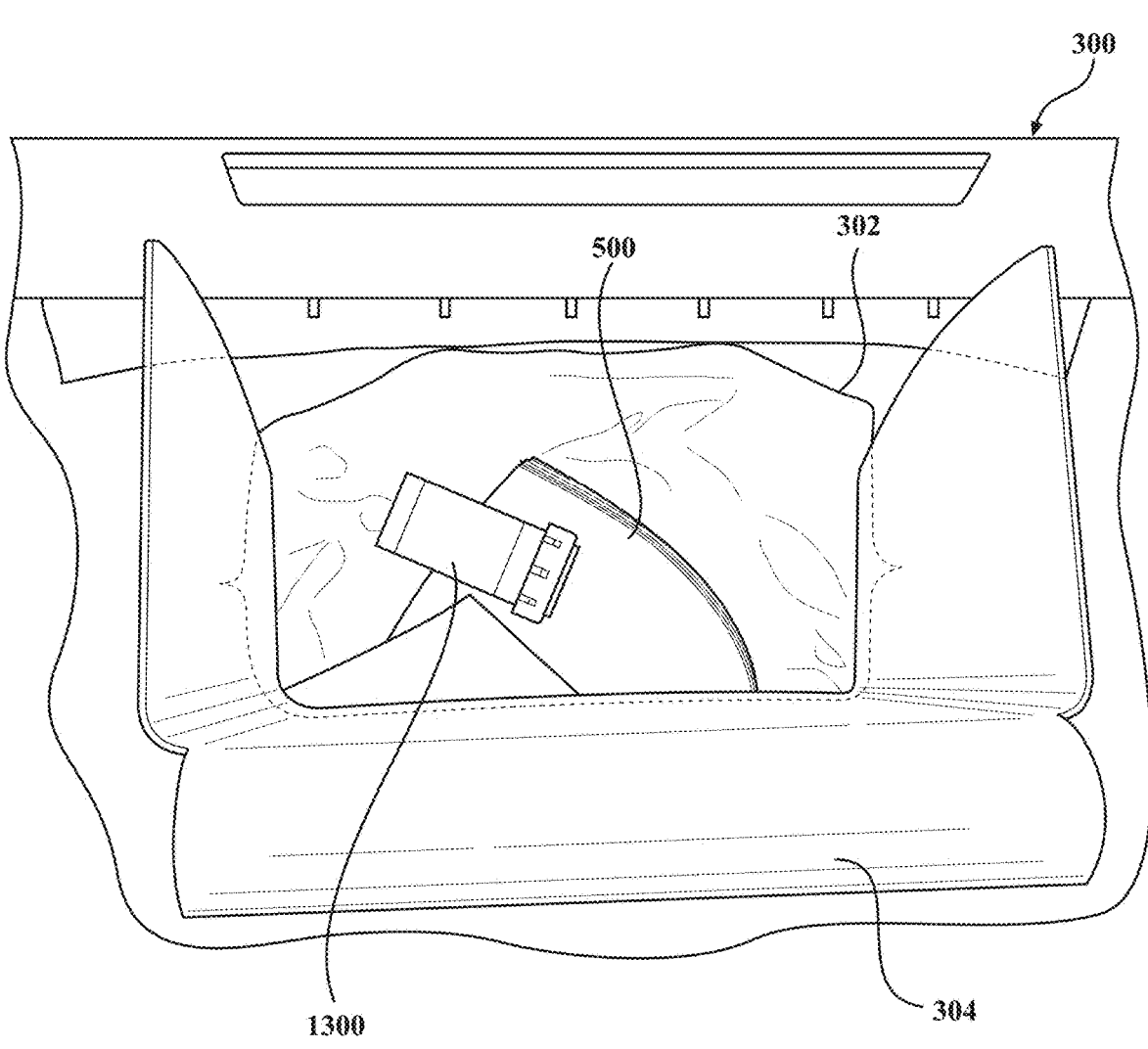
FIG. 18 a top view of a bag that new contains literature and a medication product.

Turning now to FIG. 3, the packing device 226 includes a bagger mechanism 300. The bagger mechanism 300 receives a continuous supply of unopened bags 302 from a bag source (not illustrated) and guides one of the bags 302 into a vertical orientation. In an example embodiment, the bag source includes a plurality of identically constructed bags 302 that are all connected with perforations end-to-end with one another in an elongated strip. For example, FIG. 18 shows a bag 302 that has been opened and then a portion of a "next" bag 302 to be opened and filled once the first bag 302 has been filled and sent to the shipping area. Each bag 302 in the bag source includes a pair of walls that are heat-sealed against one another along three sides to enclose an interior while leaving the top unsealed so that the bag 302 can be opened by the bagger mechanism 300. The walls of the bag 302 may include a cushioning material, such as foam or bubble wrap, for protecting the contents that is to be inserted into the bag 302 during eventual shipping of the bag 302 to an end user.

Figure 16:
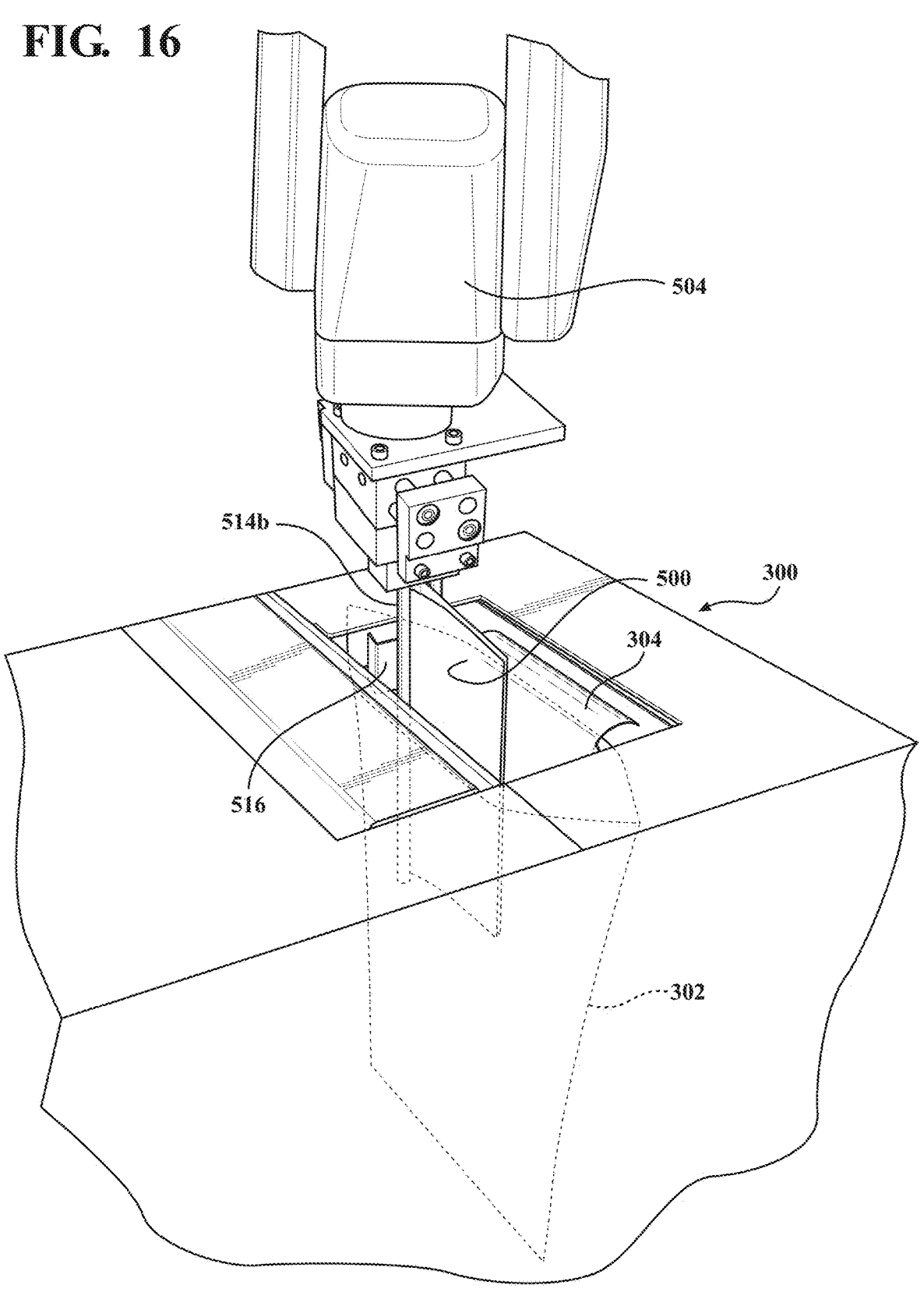
FIG. 16 is a side view showing the bagger mechanism having opened a bag prior to the insertion of the literature into the bag.

Next, the bagger mechanism 300 engages a top edge of the bag 302 and pulls the engaged top edge from an opposite top edge to open the top of the bag 302 and expose an interior of the bag 302. In the exemplary embodiment, the bagger mechanism 300 engages the top edge of the bag 302 with one or more fingers. However, any suitable engaging means may be employed, for example, one or more vacuum powered suction cups. In some embodiments, once the bagger mechanism 300 opens the top of the bag 302, it propels a burst of air into the interior of the bag 302 to enlarge the interior. However, even with the burst of air, in many cases, the bag 302 may not be fully opened at this stage. For example, as illustrated in FIG. 16, walls of the middle and bottom sections of the bag 302 may still be pressed against one another such that the exposed interior of the bag 302 is undersized.

Figure 4:
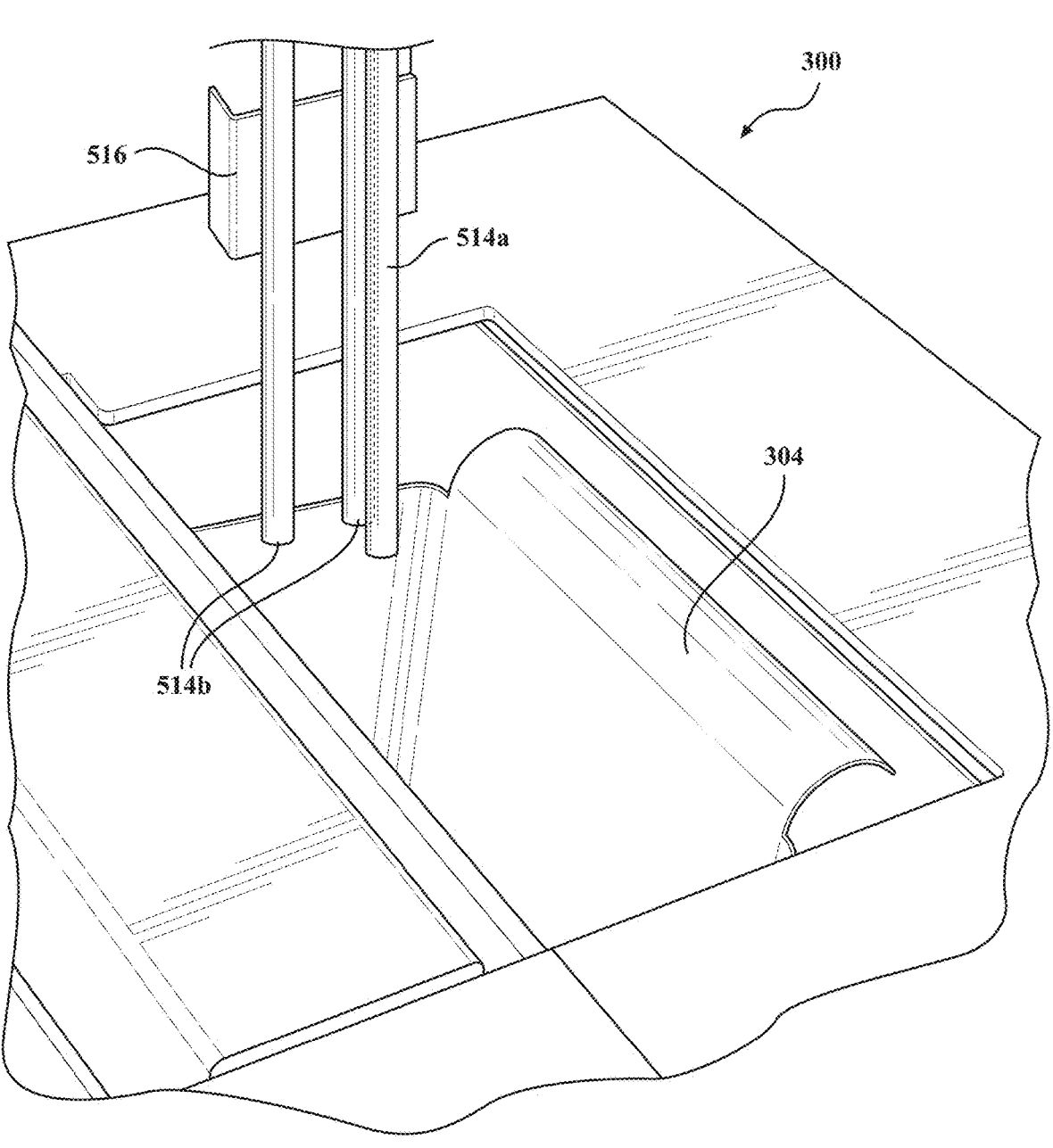
FIG. 4 is a perspective view of a bagger mechanism with a funnel disposed in an opened bag.

As illustrated in FIG. 4, once the top of the bag 302 is opened, a funnel-like guide 304 is partially inserted into the interior of the bag 302 through the opened top. The guide 304 is made as a rigid piece of material, such as plastic, and has three rigid side walls for guiding the materials (litera-ture, medications, etc.) into the bag 302, as discussed below.

Figure 5:
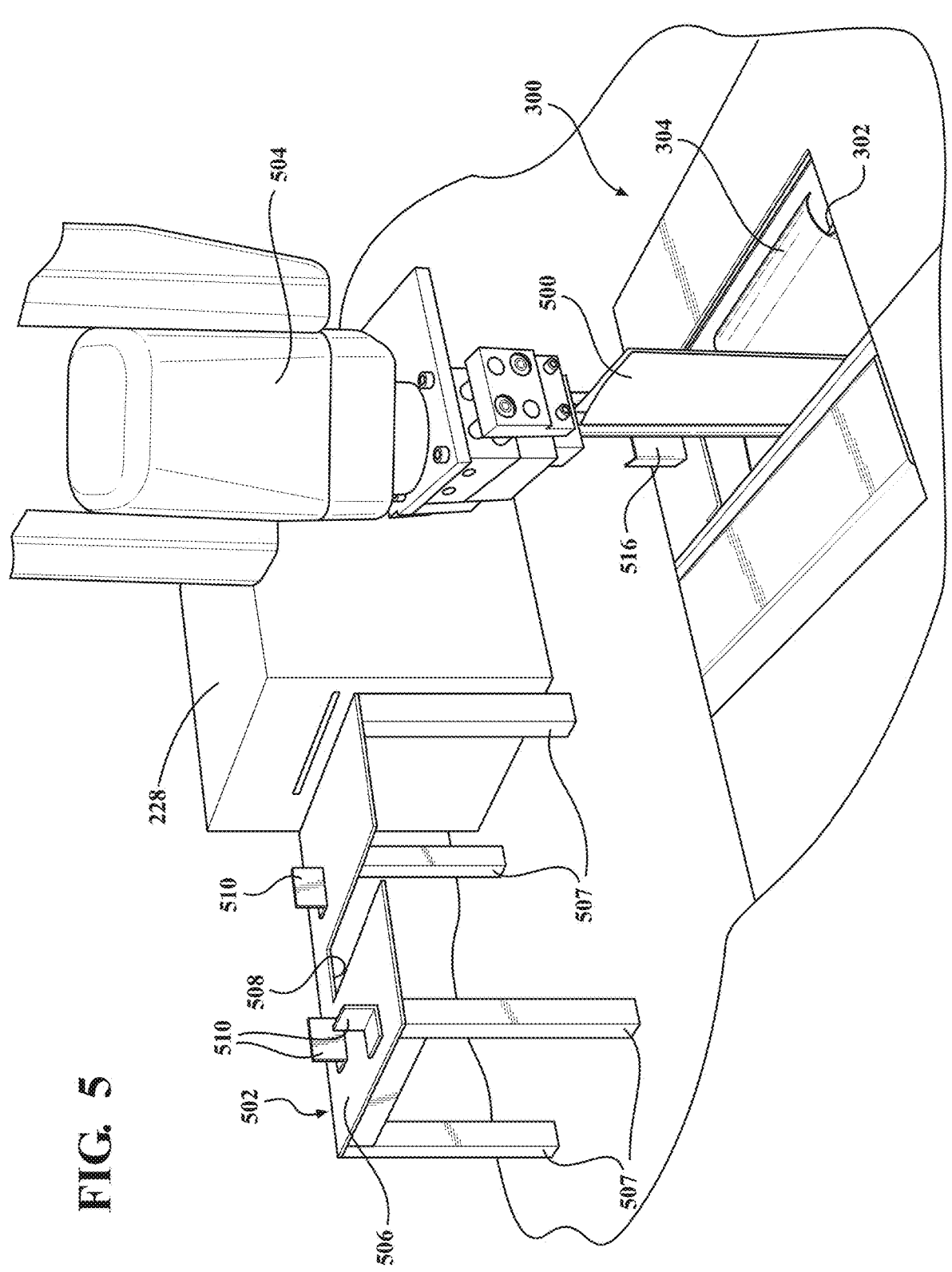
FIG. 5 is a perspective view of a packaging device including a tray with literature and a bagger mechanism.

Turning now to the environmental view of FIG. 5, the literature 500 that is produced by the literature device 228 is fed to a tray 502 that is positioned adjacent the packing device 226. In the exemplary embodiment, the literature device 228 includes a high-speed printer that is positioned immediately adjacent the tray 502 so that its output is fed directly onto the tray 502. The packing device 226 includes a robotic arm 504 that is positioned within reach of the tray 502 and the bagger mechanism 300. As discussed the following paragraphs, in operation, the robotic arm 504 engages the literature 500 and lifts it off the tray 502 and brings the literature 500 to the bagger mechanism 300. The robotic arm 504 also inserts the literature 500 into the bag 302 through the top end that is being held open by the bagger mechanism 300. In the exemplary embodiment, a second robotic arm is also positioned adjacent the bagger mecha-nism 300 for inserting the medications and any additional materials into the bag 302. In some embodiments, the medications and other materials can be inserted into the bag 302 manually. The robotic arm 504 may be able to move in six axes.

Figure 6:
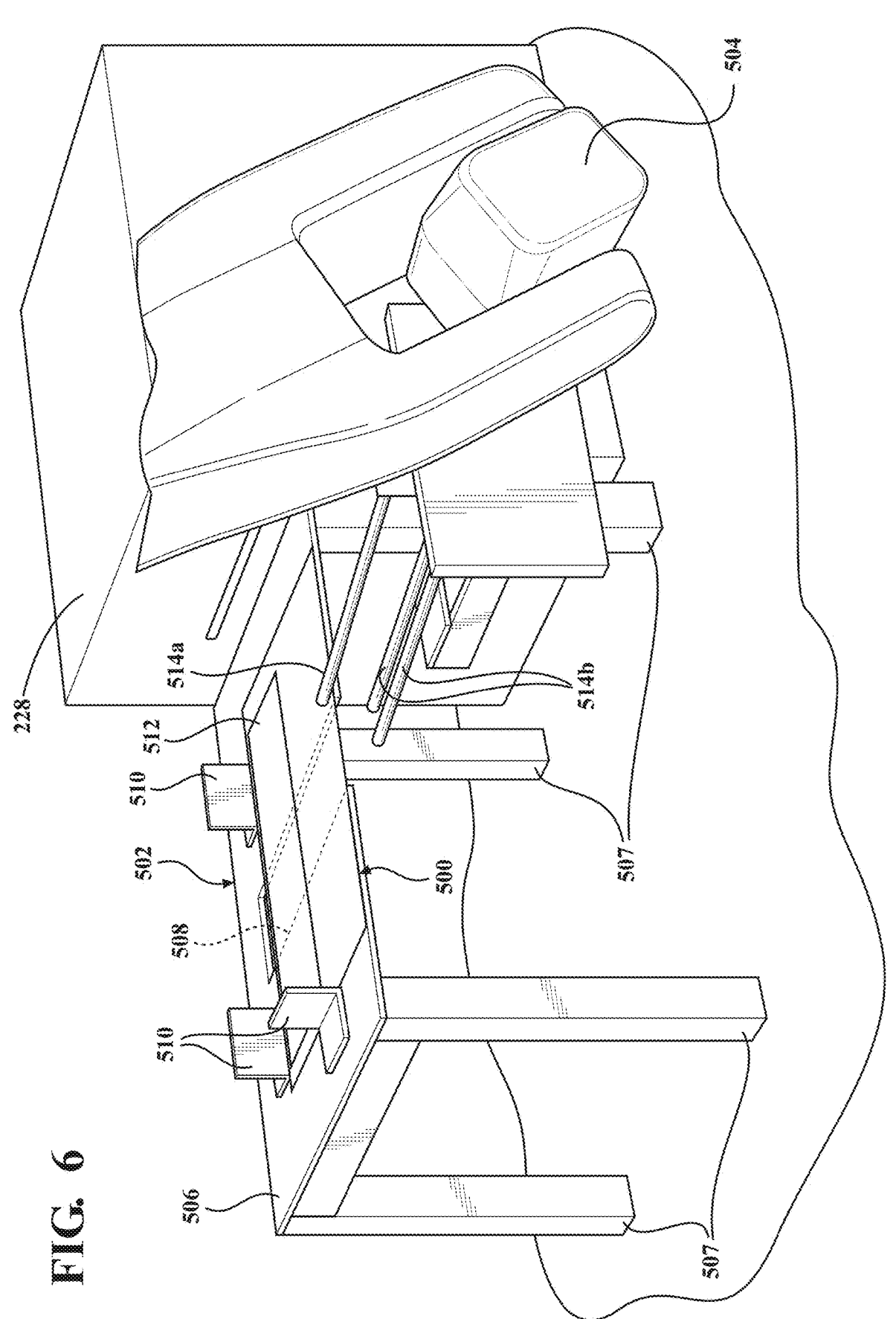
FIG. 6 is a perspective view illustrating a robotic arm in a pre-engagement position prior to engaging literature on the tray.

FIG. 6 shows the literature 500 placed on a generally flat platform 506 of the tray 502. The platform 506 is elevated by a plurality of legs 507 that extend downwardly from a periphery of the platform 506. In the exemplary embodi-ment, the platform 506 is elevated by four legs 507. The platform 506 has a gap or slot 508 formed into it at approximately a midpoint in a widthwise direction of the platform 506 and the literature 500 extends across the slot 508. The slot 508 extends from a first edge of the platform 506 and towards an opposite second edge by more than half the length of the platform 506 from the first edge to the second edge. In some embodiments, the slot 508 may extend the full distance from one edge to the other such that the platform 506 is actually made of two pieces that are spaced apart from one another by the slot 506.

A plurality of paper guides 510 are located on a top of the flat surface 506 and define a literature receiving area for holding the literature 500 in a specific location on the tray 502 such that the literature 500 extends across the slot 506. The paper guides 510 are secured with the platform 506 and extend upwardly therefrom and are spaced apart from one another at specific locations so that the papers of the literature 500 are neatly stacked on top of one another in the literature receiving area. In the exemplary embodiment, the tray 502 includes three total paper guides 510 with one of them being perpendicular to the other two 510. No paper guides 510 are found on the side of the literature receiving area that faces the literature device 228 so that the literature device 228 can output the papers of the literature 500 directly into the literature receiving area with the papers automatically contacting one of the paper guides 510 before falling into the literature receiving area. Also, no paper guides 510 are found on a side of the literature receiving area that faces first edge of the platform 506 with the slot 508 so that literature 500 in the paper receiving area can be pulled away from the tray 502 by the robotic arm 504 in this direction without the paper guides 510 impeding this action. In some embodiments, the paper guides 510 can be adjust-able or repositionable to enlarge or shrink the literature receiving area so that it can accommodate different sizes and/or different shapes of literature 500. In some embodi-ments, the tray 502 may also include one or more openings or additional slots on either side of the slot 508 to allow air to escape from beneath the literature 500 as the literature 500 settles from the literature device onto the tray.

In some embodiments, the multiple trays may be provided that can share a common literature device or have their own unique literature devices so that the robotic arm can pick literature from one try while another tray is being loaded with literature. In some other embodiments, the tray can include multiple surfaces adjacent one another and con-nected via one or more conveyors that can stage the litera-ture prior to picking.

The paper guides 510 extend vertically high enough to accommodate any suitable numbers of papers. In the exem-plary embodiment, the literature 500 includes a plurality of papers (for example, 1-12 papers in some embodiments) and an unsealed return envelope 512. The papers may include any suitable information including, for example dosage instructions, medication safety directions, medication warn-ings, etc. The envelope 512 is oriented laterally so that it also extends across the slot 508 in the platform 506 when the literature 500 is in the literature receiving area of the tray 502. In the exemplary embodiment, the envelope 512 is placed on top of the papers within the literature receiving area. In some embodiments, the literature 500 can include more than one envelop 512 (for example, two envelopes).

Figure 15A:
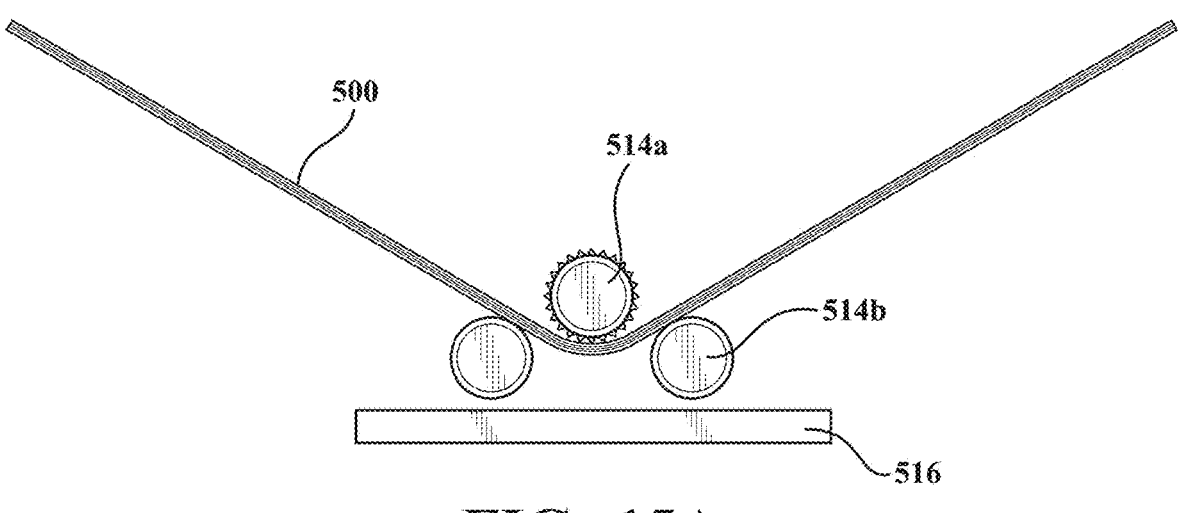
FIG. 15A is a front view showing a plurality of fingers of the robotic arm in barely engaged positions (close to the disengaged positions)
Figure 15B:
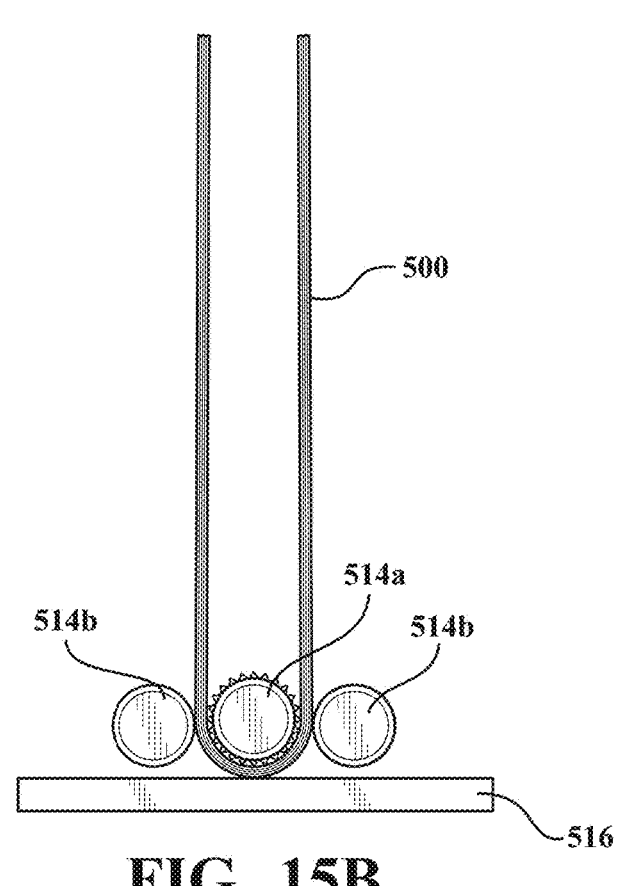
FIG. 15B is a front view showing the plurality of fingers of the robotic arm in the engaged positions.

The slot 508 extends to an edge of the platform 506 that faces towards the robotic arm 504. An end of the robotic arm 504 includes a literature grabbing mechanism which consists of three fingers 514a, 514b, including a central finger 514a and two outer fingers 514b, that all extend parallel with one another in a first direction. The fingers 514*a*, 514*b* are operably connected with respective actuators (shown schematically in FIG. 19) that can move at least fingers 514*a*, 514*b* relative to the others. Specifically, with respect to the orientations of the fingers in FIGS. 15A and 15B, the literature grabbing mechanism is able to move the central finger 514*a* from a disengaged position above the outer fingers 514*b* downwardly to an engaged position where the central finger 514*a* is aligned with or nearly aligned with the outer fingers 514*b*. In some embodiments, the literature grabbing mechanism may be configured to move the outer fingers 514*b* and not the central finger 514*a* or may be configured to move all of the fingers 514*a*, 514*b*. The at least one finger 514*a*, 514*b* that is movable moves in a second direction that is perpendicular to the first direction. The actuators may be electrically actuated, pneumatically actuated, or may be actuated through any suitable means. In an exemplary embodiment, the fingers 514*a*, 514*b* are made of metal, such as steel, an alloy steel, aluminum, or an aluminum alloy. However, in some embodiments, the fingers 514*a*, 514*b* may be made of other materials, including plastics.

Turning back to FIG. 5, the fingers 514*a*, 514*b* all have similar lengths, which is approximately equal to a height of the papers of the literature 500 so that the entire height of the literature 500 can be engaged by the fingers 514*a*, 514*b*. In some embodiments, the fingers 514*a*, 514*b* can be longer than the height of the literature 500 or can be slightly shorter than the height of the literature 500.

In FIG. 6, the literature grabbing mechanism is shown in a pre-engagement position where it is positioned in front of the slot 508 of the platform 506. The fingers at this point are in their disengaged positions, whereby the single central finger 514*a* is positioned vertically above and laterally between the two outer fingers 514*b*. In the vertical direction, the platform 506 and the literature 500 are located between the central and outer fingers 514*a*, 514*b*. As illustrated, the fingers 514*a*, 514*b* all extend in parallel with the slot 508 and in a horizontal direction. The slot 508 has a width that is greater than a width of the central finger 514*a*. In an embodiment where the outer fingers 514 move relative to the central finger 514*a*, then the width of the slot 508 must be greater than a distance between the outer fingers 514*b*.

Figure 7:
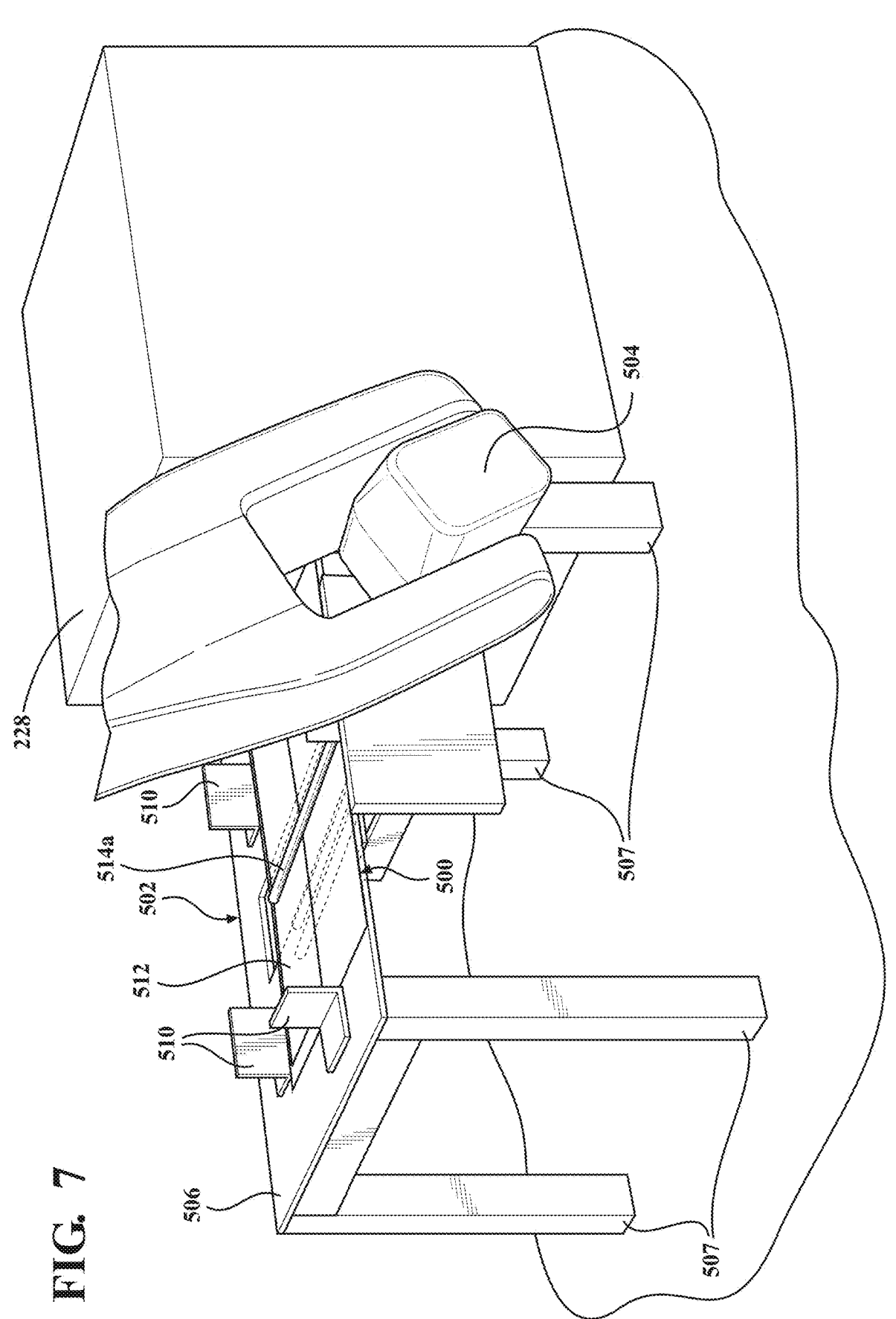
FIG. 7 is a perspective view of the robotic arm immediately prior to engaging the literature on the tray.

Next, the robotic arm 504 moves the literature grabbing mechanism forwardly to the location shown in FIG. 7 where the central finger 514*a* is directly above the literature 500 and the outer fingers (hidden in this view) are directly below the literature 500. The literature grabbing mechanism is now ready to be activated to engage the fingers 514*a*, 514*b* with literature 500.

Figure 8:
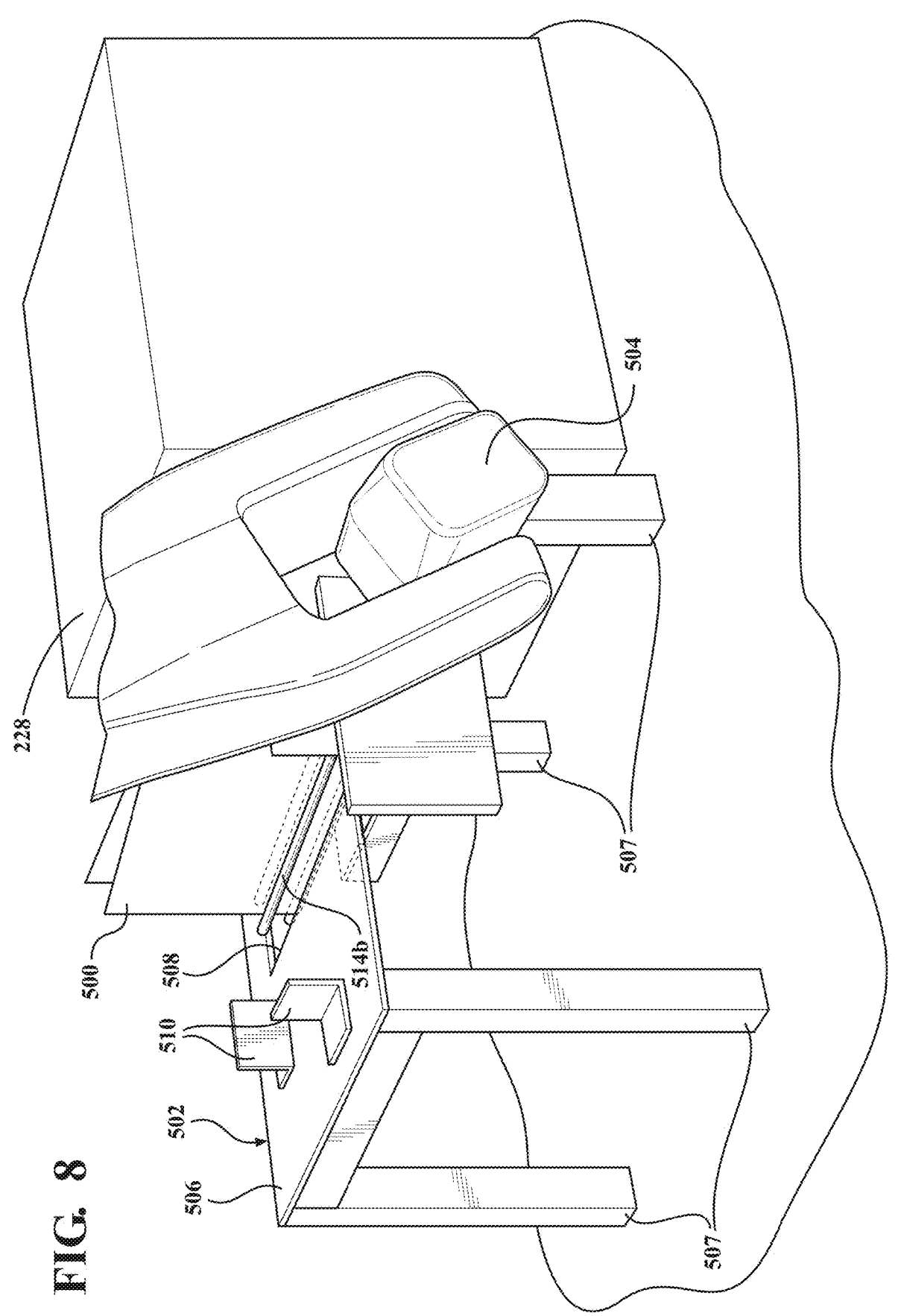
FIG. 8 is a perspective view of the robotic arm after having engaged the literature on the tray.

Turning now to FIG. 8, in the exemplary embodiment, the central finger 514*a* (hidden in this view) is then actuated and moved vertically downwardly towards and either in alignment with or past the outer fingers 514*b*. At this time, the central finger 514*a* passes through the slot 508 from above the platform 506 to below the platform 506. The fingers 514*a*, 514*b* are now in their engaged positions, and the movement of the fingers 514*a*, 514*b* from the disengaged configuration to the engaged configuration has caused the literature 500 to fold approximately in half around the central finger 514*a* without creasing the papers of the literature 500. Creasing of the literature 500 is avoided because the curvature at the fold is dictated by the curvature of an outer surface of the central finger 514*a*. As illustrated, when folded, the opposing edges of the literature 500 either contact one another or nearly contact one another, i.e., within one inch (1") of touching. Thus, the literature 500 is folded by either one hundred and eighty degrees (180°) or nearly one hundred and eighty degrees, e.g., at least one hundred and seventy degrees (170°).

At this point, the literature grabbing mechanism is tightly engaged with the literature 500 by way of friction between the literature 500 and the fingers 514*a*, 514*b*. In an exemplary embodiment, outer surfaces of one or more of the fingers 514*a*, 514*b* may be knurled or otherwise textured to increase the friction between the fingers 514*a*, 514*b* and the literature 500 and establish a more resilient engagement between the literature 500 and the literature grabbing mechanism as compared to smooth fingers. For example, in one embodiment, the knurling is only provided on the central finger 514*a*. In some embodiments, other gripping means rather than knurling may be employed to increase friction between the fingers 514*a*, 514*b* and the literature 500. For example, in some embodiments, one or more foam or rubber rings can be placed on one or more of the fingers 514*a*, 514*b* to improve friction between the literature 500 and the fingers 514*a*, 514*b*.

Figure 9:
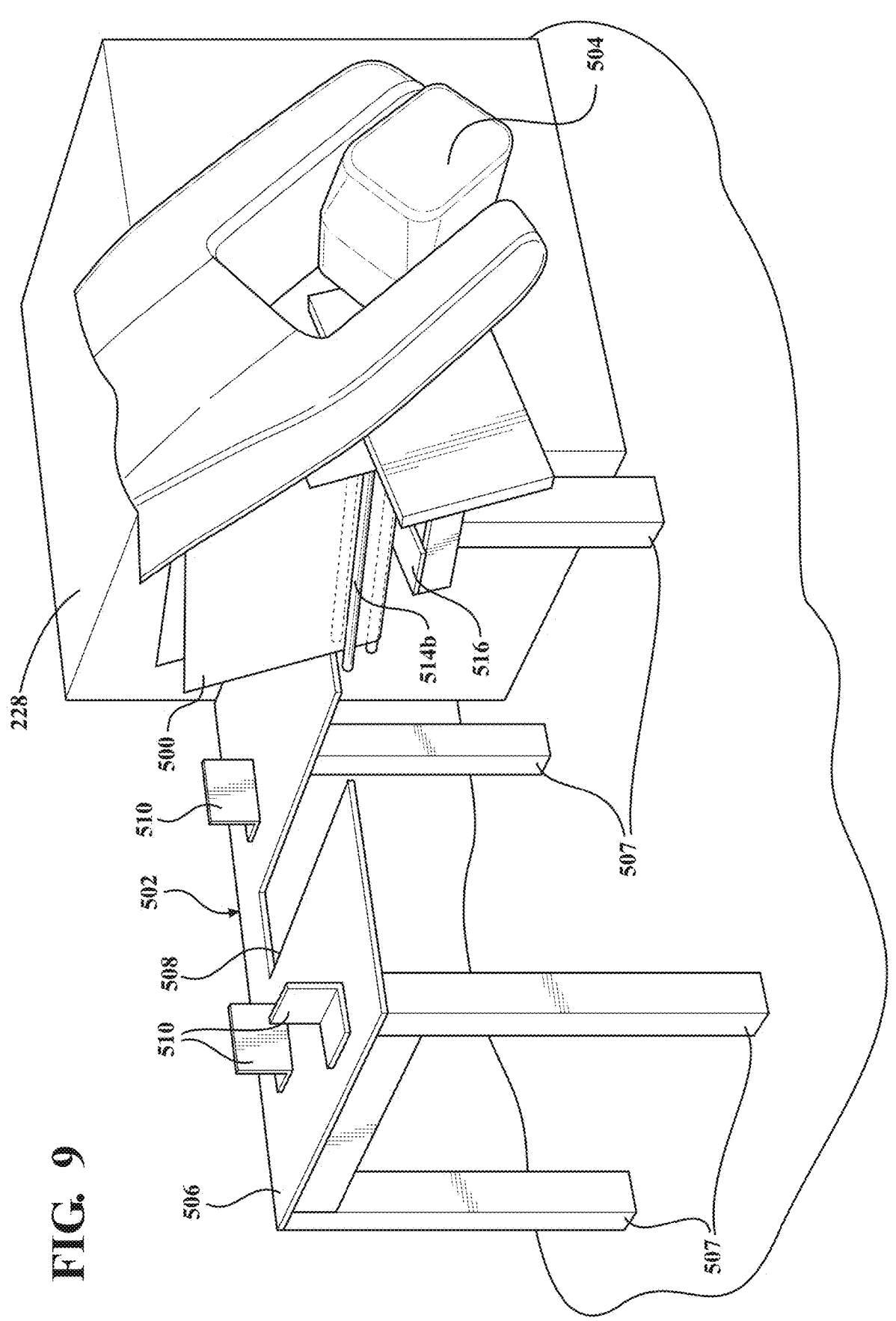
FIG. 9 is a perspective view of the robotic arm beginning to remove the literature from the tray.

Turning now to FIG. 9, once the literature 500 has been sufficiently gripped by the fingers 514*a*, 514*b*, the robotic arm 504 pulls the literature 500 away from the platform 506. Due to the strong frictional engagement between the fingers 514*a*, 514*b* and the literature 500, the robotic arm 504 can pull the literature 500 at a rapid speed away from the tray 502 in a direction parallel to the fingers 514*a*, 514*b*, i.e., the robotic arm 504 does not have to first raise the literature 500 prior to removing it from the platform 506.

Figure 10:
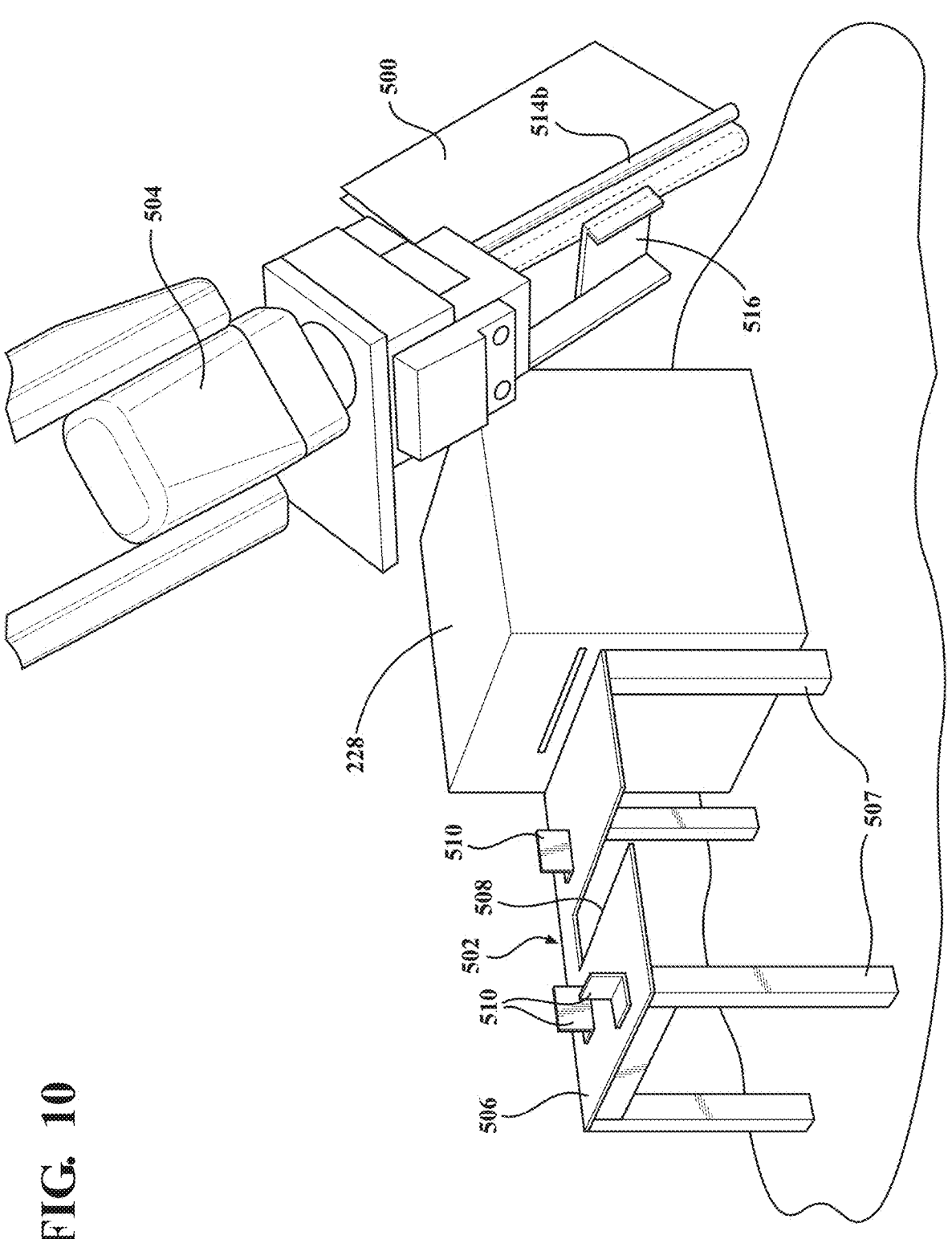
FIG. 10 is a perspective view of the robotic arm transporting the literature from the tray to the bagger mechanism.

FIG. 10 shows the robotic arm 504 carrying the literature 500 from the tray 502 towards the bagger mechanism 300. As illustrated, at this stage, the robotic arm 504 has begun to rotate the fingers 514*b* (514*a* is hidden in this view) and the literature 500 towards a vertical orientation. As also illustrated, the literature grabbing mechanism includes a stop 516 (or step) that contacts the literature 500 at the fold to further assist in holding the literature 500 on the grabbing mechanism at the end of the robotic arm 504. In the exemplary embodiment, the stop 516 has the form of a plate that is spaced from the fingers 514*a*, 514*b*. When the fingers 514*a*, 514*b* are in in the engaged configuration, the fold of the literature 500 is sandwiched between the central finger 514*a* and the stop 516. The stop 516 is located approximately at a halfway point along the length of the fingers 514*a*, 514*b*. When the central finger 514*a* moves from the disengaged position to the engaged position, it moves towards the stop 516 to sandwich the literature 500 between the central finger 514*a* and the stop 516. The stop 516 may also assist in pushing the literature 500 out of the robotic arm as the central finger 514*a* disengages, as described in further detail below.

Figure 11:
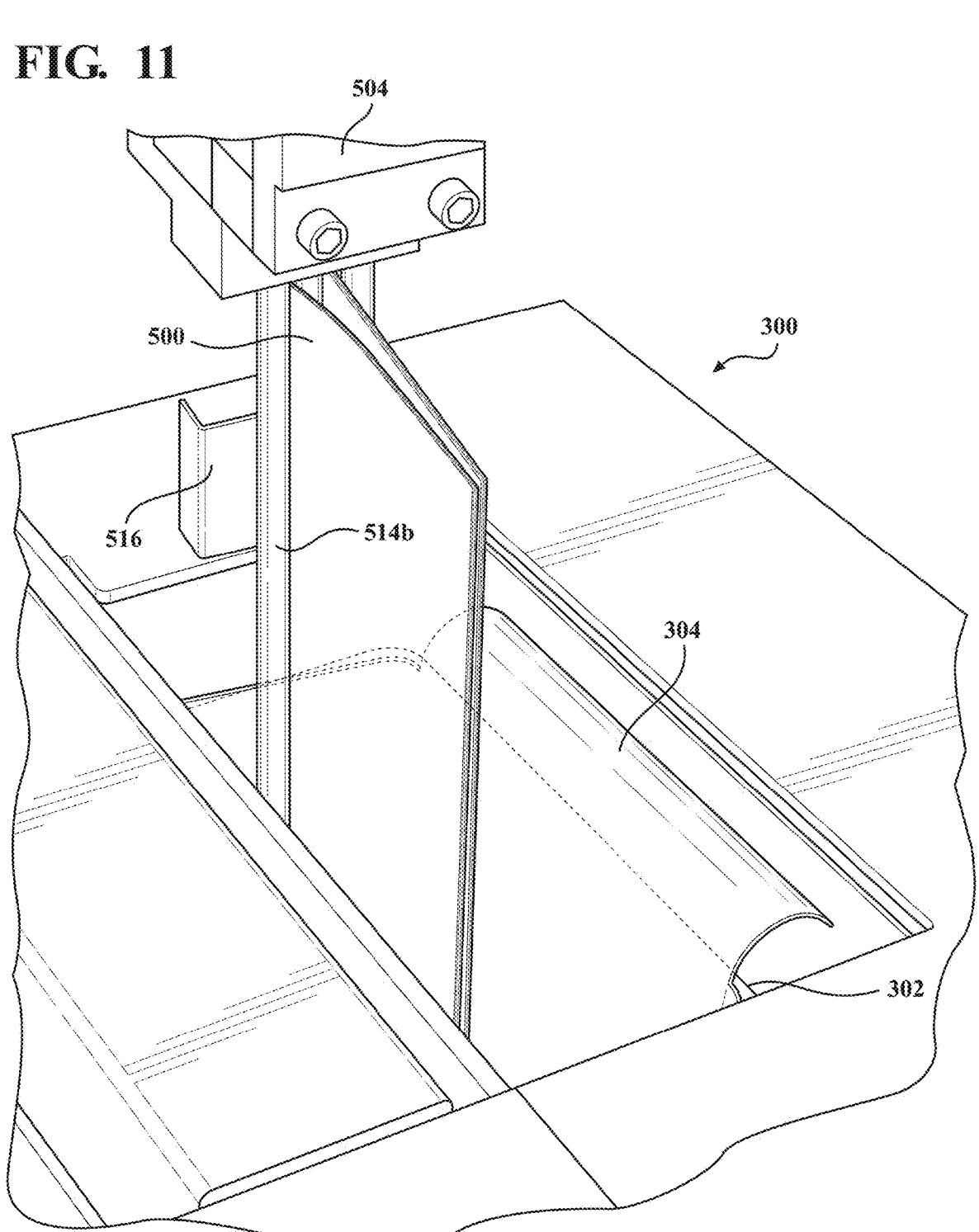
FIG. 11 is a perspective view of the robotic arm prior to inserting the literature into the bag at the bagger mechanism.

Turning now to FIG. 11, the robotic arm 504 has now brought the literature 500 to the bagger mechanism 300 and has fully rotated the literature grabbing mechanism such that the fingers 514*a*, 514*b* extend vertically. Because the fingers 514*a*, 514*b* (central finger 514*a* is hidden in this view) are in the engaged configuration, friction between the literature 500 and the fingers 514*a*, 514*b* still holds the literature 500. The robotic arm 504 positions the literature 500 directly above the open bag 302 and the guide 304. The robotic arm 504 then moves the literature 500 directly vertically downwardly into the bag 302 with all three of the fingers 514*a*, 514*b* extending past the open top of the bag 302 and into the interior of the bag 302. In an example embodiment, the robotic arm 504 moves downwardly until the literature and the ends of the fingers 514*a*, 514*b* are more than halfway from the open top towards a closed bottom of the bag 302.

More specifically, in an example embodiment, the ends of the fingers 514a, 514b extend at least six inches (6") into a bag 302 from the open top end of a ten-by-thirteen inch (10"×13") bag 302. In this embodiment, the literature 500 includes eight and a half-by-eleven inch (8.5"×11") paper. Thus, in this example, greater than seventy percent (70%) of the literature 500 is directly inserted by the robotic arm 504 into the bag 302 prior to the robotic arm 504 releasing the literature 500.

Figure 12:
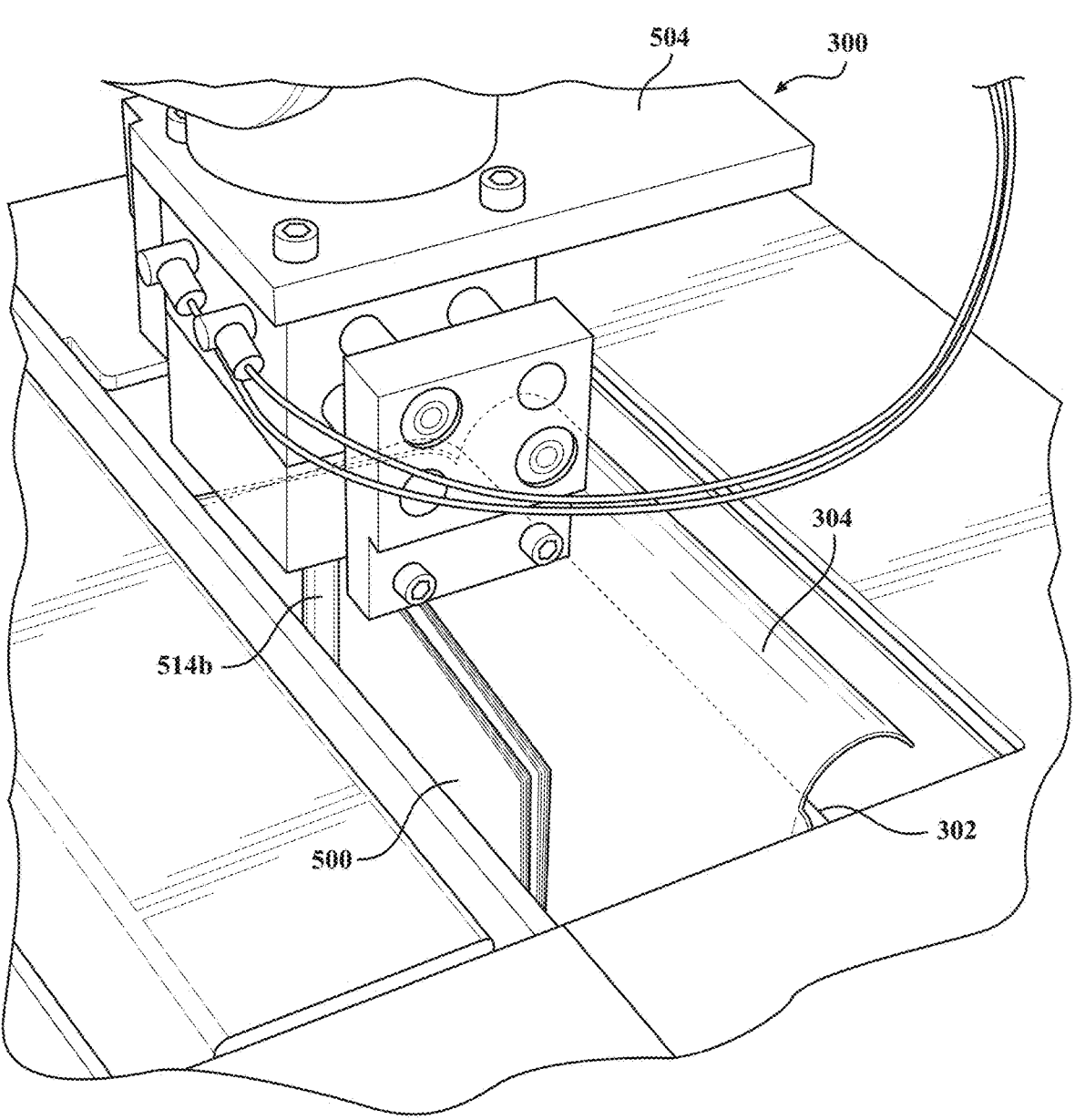
FIG. 12 is a perspective view showing the robotic arm inserting the literature into the bag.
Figure 17:
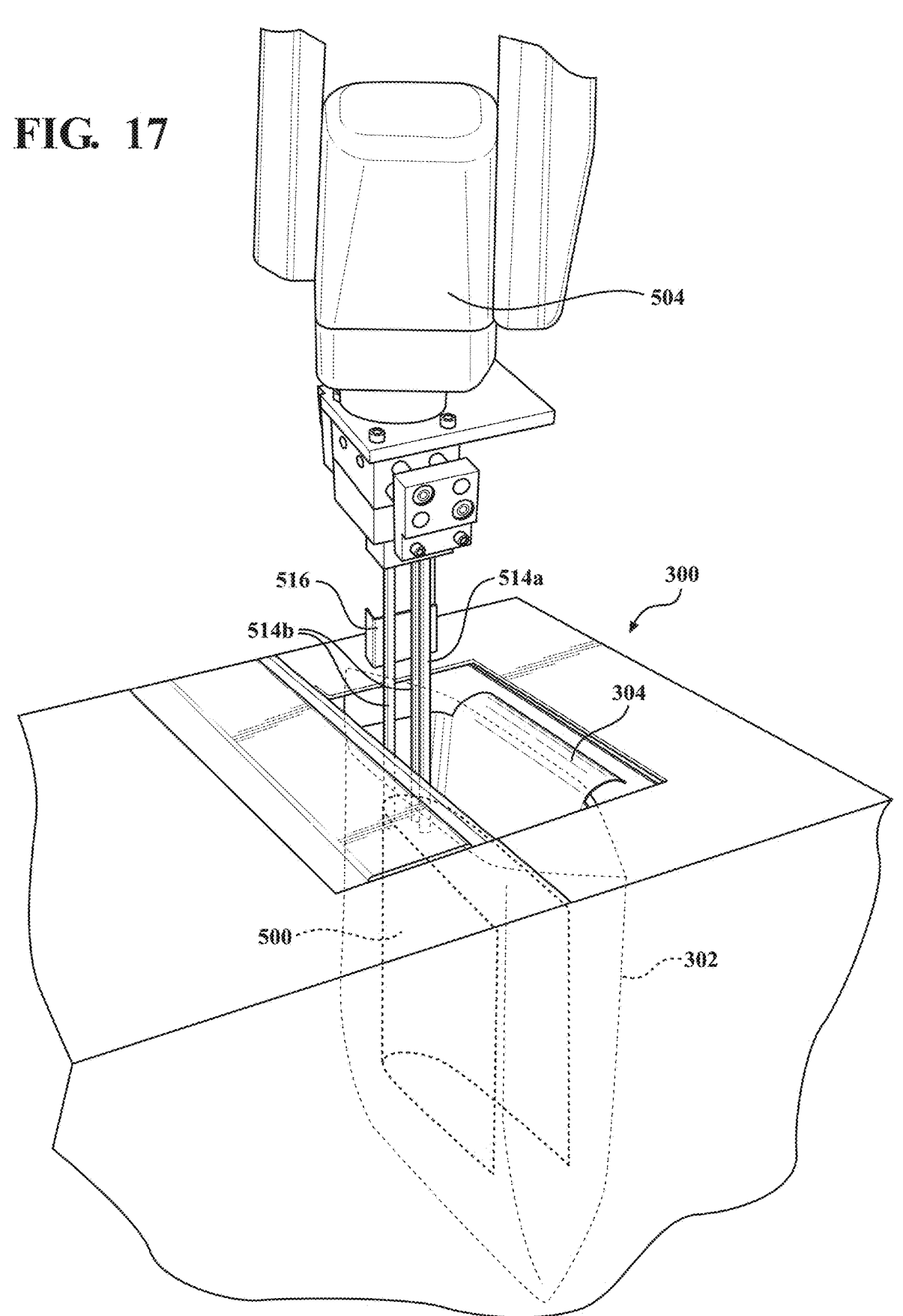
FIG. 17 is a side view showing the robotic arm having inserted the literature into the bag.

As the robotic arm 504 urges the literature 500 downwardly into the bag 302, the literature 500 has the effect of opening the middle and bottom sections of the bag 302, which were previously still substantially closed. FIG. 17 illustrates the bag 302 now being opened along its length by way of the robotic arm 504 inserting the literature 500 (hidden in this view) deeply into the bag 302. The guide 304 may assist in ensuring that the literature 500 is properly inserted into the interior of the bag 302 by the robotic arm 504. In FIG. 12, the robotic arm 504 has moved the literature 500 most of the way into the bag 302. The fingers 514a, 514b (hidden in this view) are nearly completely in the bag 302 and are still in the engaged configuration holding the literature 500.

Figure 13:
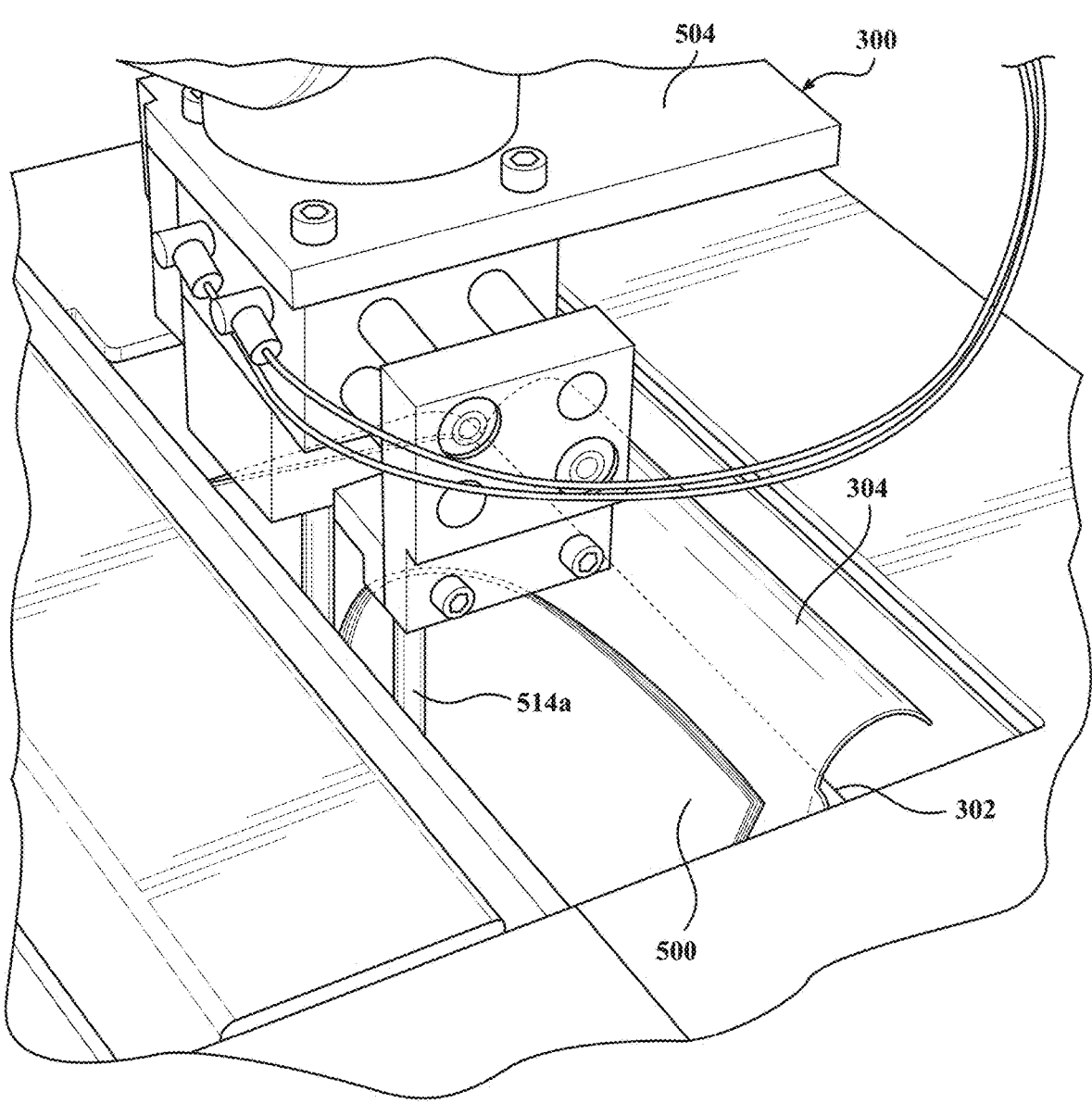
FIG. 13 is a perspective view showing the robotic arm having just released the literature.

Next, the central finger 514a is moved by the actuator to the disengaged configuration to release the literature 500 from the literature grabbing mechanism and the robotic arm 504 removes the fingers 514a, 514b from the bag 302. As illustrated in FIGS. 13 and 18, with the fingers 514a, 514b no longer engaging the literature 500, the literature 500 naturally springs outwardly slightly, thereby exposing a passage between the halves of the literature 500 on opposite sides of the non-creased fold. Bottles 1300 or packages containing the medication(s) or any other suitable items can be inserted into the bag 302 through the passage at this time. In other words, the literature 500 holds the bag 302 open so that the other components of the delivery can be more easily inserted into the bag 302. If the literature 500 holds its shape after the fingers 514a, 514b disengage, the stop 516 can assist in disengaging the literature 500 from the robotic arm 504.

Turning back to FIG. 5, a second robotic arm 518 may be provided adjacent the bagger mechanism 300 and configured to pick bottles 1300 from a medication area or any other type of medication container and/or accessory and place those components in the bag 302 while the bag 302 is being held open by the literature 500 inside it. In some embodiments, additional robotic arms may also be provided to quickly fill the bag 302 once it is being held open by the literature 500.

Figure 14:
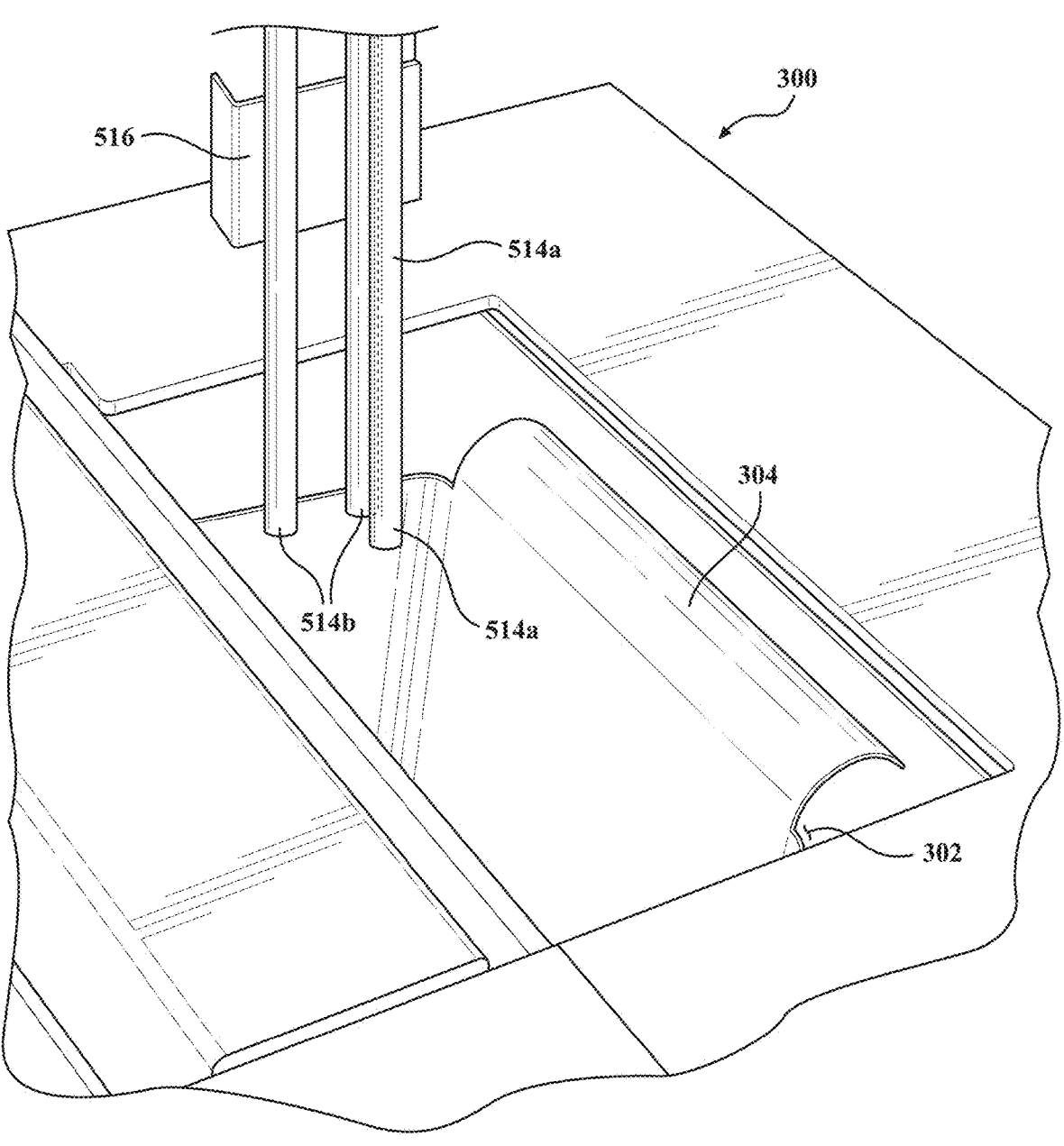
FIG. 14 is a perspective view showing the robotic arm having been removed from the bag.

Turning now to FIG. 14, the bagger mechanism 300 pulls the filled bag away and towards the shipping location. A next bag 302 can then be moved into the filling position by the bagger mechanism 300.

With this, the aforementioned process can restart, i.e., the bagger mechanism 300 opens a new bag 302, the robotic arm 504 grabs new literature 500 and places it in the bag 302, etc. In some embodiments, any two or more of the above-discussed steps can be performed simultaneously with one another. For example, the robotic arm 504 can be grabbing the literature 500 simultaneous to the bagger mechanism 300 opening the bag 302.

Figure 19:
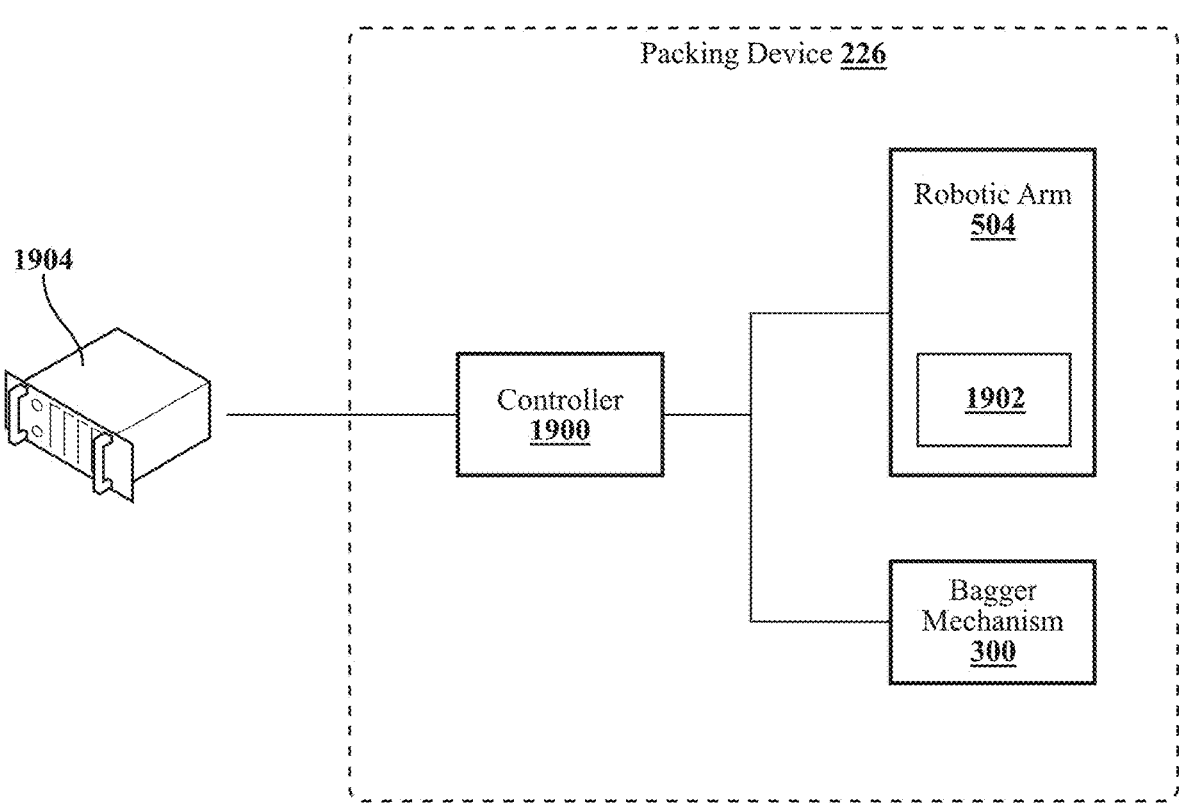
FIG. 19 is a black box view of the packing device.

FIG. 19 is a schematic diagram of the packing device 226. The packing device includes a controller 1900 that is in electrical communication with the robotic arm 504, including the actuators 1902 that control movement of the fingers for controlling the picking of the literature off of the tray and the placement of the literature into the bags. The controller 1900 is also in electrical communication with the bagger mechanism 300 for controlling the opening of the bags so that the literature can be inserted into the bags. The controller 1900 includes at least one processor, at least one memory, and at least one communications interface. Upon receiving an instruction from a remote server 1904, the controller can automatically pick the literature from the tray and, using the same motion for each instance, place the literature into an open bag. This process can be repeated at a high frequency to fill many bags with literature and products prior to shipping.

Another aspect of the present disclosure is related to a method of filling a medication package in the form of a bag 302 with medications and literature. FIG. 20 is a flow chart that depicts the steps of filling a bag 302 according to an example embodiment. At step 2000, the bagger mechanism 300 opens a top of the bag 302. At step 2002, the robotic arm 504 moves the literature grabbing mechanism such that the central finger 514a is positioned directly above the literature 500 on the tray 502. At step 2004, the fingers 514a, 514b are moved from the disengaged configuration to the engaged configuration. This may involve moving the central finger 514a from above the platform 506 through the slot to below the platform 506 such that the literature 500 automatically folds around the central finger 514a due to the positions of the outer fingers 514b. At step 2006, the robotic arm 504 removes the literature 500 from the tray 502 and carries the literature 500 to the bagger mechanism 300.

At step 2008, the robotic arm 504 inserts the literature 500 into the bag 302. In some embodiments, the literature 500 is inserted by the robotic arm 504 over halfway into the bag 302 before the robotic arm 504 releases the literature 500. In some other embodiments, the literature 500 is inserted by the robotic arm 504 over seventy percent (70%) of the way into the bag 302 before the robotic arm 504 releases the literature 500. At step 2010, the robotic arm 504 releases the literature 500 by moving the fingers 514a, 514b from the engaged position to the disengaged position. The literature 500 will naturally spring partially outwardly to further open the bag 302 and present a passage. At step 2012, additional products (for example, a bottle 1300 containing medications) are inserted into the passage of the bag 302.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method can be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements but can also be an indirect relationship where one or more intervening elements are present (either spatially or functionally) between the first and second elements.

As used herein, the phrase at least one of A, B, and C should be construed to mean a logical (A OR B OR C), using a non-exclusive logical OR, and should not be construed to mean "at least one of A, at least one of B, and at least one of C." The term subset does not necessarily require a proper subset. In other words, a first subset of a first set can be coextensive with (equal to) the first set.

In this application, including the definitions below, the term "module" or the term "controller" can be replaced with the term "circuit." The term "module" can refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module or other physical element in the pharmacy system can include one or more interface circuits. In some examples, the interface circuit(s) can implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4. For example, the interface circuits allow the robots to communicate with a controller, with each other or with other devices.

The module or controller can communicate with other modules using the interface circuit(s). Although the module can be depicted in the present disclosure as logically communicating directly with other modules, in various implementations the module can actually communicate via a communications system. The communications system includes physical and/or virtual networking equipment such as hubs, switches, routers, and gateways. In some implementations, the communications system connects to or traverses a wide area network (WAN) such as the Internet. For example, the communications system can include multiple LANs connected to each other over the Internet or point-to-point leased lines using technologies including Multiprotocol Label Switching (MPLS) and virtual private networks (VPNs).

In various implementations, the functionality of the module can be distributed among multiple modules that are connected via the communications system. For example, multiple modules can implement the same functionality distributed by a load balancing system. In a further example, the functionality of the module can be split between a server (also known as remote, or cloud) module and a client (or, user) module.

Some or all hardware features of a module can be defined using a language for hardware description, such as IEEE Standard 1364-2005 (commonly called "Verilog") and IEEE Standard 1076-2008 (commonly called "VHDL"). The hardware description language can be used to manufacture and/or program a hardware circuit. In some implementations, some or all features of a module can be defined by a language, such as IEEE 1666-2005 (commonly called "SystemC"), that encompasses both code, as described below, and hardware description.

The term code, as used above, can include software, firmware, and/or microcode, and can refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The robots described herein include memory circuits to store control instructions and order information. The term computer-readable medium, as used herein, does not encompass transitory electrical or electromagnetic signals propagating through a medium (such as on a carrier wave); the term computer-readable medium can therefore be considered tangible and non-transitory. Non-limiting examples of a non-transitory computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application can be partially or fully implemented by a special purpose computer created by configuring a computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The processors can control the robots, or any other device described herein. The computer programs can also include or rely on stored data. The computer programs can encompass a basic input/output system (BIOS) that interacts with hardware of the special purpose computer, device drivers that interact with particular devices of the special purpose computer, one or more operating systems, user applications, background services, background applications, etc.

The computer programs can include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code can be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A medication packaging system, comprising:
   a tray with a slot and a literature receiving area that is configured to hold literature in a position above the slot; and
   a robotic arm extending to a distal end that has a literature grabbing mechanism, the literature grabbing mechanism including a plurality of fingers that extend parallel to one another in a first direction, the plurality of fingers including a central finger and a pair of outer fingers that are located on opposite sides of the central finger,
   at least one of the central and outer fingers being movable in a second direction that is perpendicular to the first direction between a disengaged position on one side of the slot of the tray to an engaged position at least partially on another side of the slot to engage and fold the literature in the literature receiving area of the tray,
   the system configured to operate by:
      disposing the literature in the literature receiving area of the tray and across the slot of the tray;
      bringing the literature grabbing mechanism at the distal end of the robotic arm to the tray, positioning the central finger of the literature grabbing mechanism directly above the literature, and positioning the two outer fingers of the literature grabbing mechanism directly below the literature; and
      moving at least one of the central and outer fingers towards at least one of the other fingers in the second direction that is perpendicular to the first direction and at least partially through the slot of the tray to cause the literature to fold around the central finger.

2. The medication packaging system as set forth in claim 1, wherein the central finger is movable relative to the outer fingers.

3. The medication packaging system as set forth in claim 2, wherein the literature grabbing mechanism further includes a stop device that is spaced from the plurality of fingers, and
   wherein movement of the central finger in the second direction from the disengaged position to the engaged position is towards the stop device to trap the literature between the central finger and the stop device.

4. The medication packaging system as set forth in claim 1, further including a bagger mechanism that is configured to open a top of a bag.

5. The medication packaging system as set forth in claim 4, further including a controller, the controller being configured to activate the robotic arm to:
   engage the literature in the literature receiving area of the tray with the plurality of fingers, and
   insert the literature into the bag that has been opened by the bagger mechanism.

6. The medication packaging system as set forth in claim 5, wherein the controller is further configured to activate the robotic arm to:
   rotate the literature from a first orientation that the literature has immediately after the fingers engage the literature to a second orientation that is perpendicular to the first orientation prior to inserting the literature into the bag.

7. The medication packaging system as set forth in claim 6, wherein the controller is further configured to activate the robotic arm to:
   insert at least six inches of the literature into the bag prior to disengaging the literature and removing the fingers from the bag.

8. The medication packaging system as set forth in claim 5, wherein the controller is further configured to activate the robotic arm to:
   slide the literature from the literature receiving area of the tray in a horizontal direction.

9. A method of filling a medication package, comprising the steps of:
   disposing at least one sheet of literature in a literature receiving area of a tray and across a slot of the tray;
   bringing a literature grabbing mechanism at a distal end of a robotic arm to the tray and positioning at least one central finger of the literature grabbing mechanism directly above the at least one sheet of literature and positioning at least two outer fingers of the literature grabbing mechanism directly below the at least one sheet of literature, the fingers extending in parallel relationship with one another in a first direction; and
   moving at least one of the fingers towards at least one of the other fingers in a second direction that is perpendicular to the first direction and at least partially through the slot of the tray to cause the at least one sheet of literature to fold around the at least one central finger.

10. The method as set forth in claim 9, wherein the at least one central finger includes only a single central finger.

11. The method as set forth in claim 10, wherein the step of moving at least one of the fingers towards at least one of the other fingers in the second direction includes moving the single central finger towards the outer fingers while the outer fingers remain stationary.

12. The method as set forth in claim 11, wherein the literature grabbing mechanism further includes a stop device, and wherein the method further includes the step of:
   sandwiching portions of the at least one sheet of literature between the single central finger and the stop device.

13. The method as set forth in claim 9, further including the step of opening a top of a bag with a bagger mechanism.

14. The method as set forth in claim 13, further including the steps of:
   removing the at least one sheet of literature from the tray with the robotic arm; and
   bringing the at least one sheet of literature from the tray to the bagger mechanism with the robotic arm.

15. The method as set forth in claim 14, further including the step of inserting the at least one sheet of literature into the bag with the robotic arm.

16. The method as set forth in claim 15, wherein the step of inserting the at least one sheet of literature into the bag with the robotic arm includes inserting a majority of the at least one sheet of literature into the bag and then further opening the bag with the at least one sheet of literature prior to disengaging the fingers of the literature grabbing mechanism from the at least one sheet of literature.

17. The method as set forth in claim 16, further including the step of rotating the at least one sheet of literature from a first orientation to a second orientation with the robotic arm during the step of bringing the at least one sheet of literature from the tray to the bagger mechanism.

18. The method as set forth in claim 17, further including the step of inserting a medication into the bag.

19. A high-volume pharmacy, comprising:

a bagger mechanism configured to receive a bag from a bag source and open a top of the bag;

a tray with a slot and a literature receiving area that is configured to hold literature in a position above the slot;

a robotic arm extending to a distal end that has a literature grabbing mechanism, the literature grabbing mechanism including a plurality of fingers that extend parallel to one another in a first direction, the plurality of fingers including a central finger and a pair of outer fingers that are located on opposite sides of the central finger, the central finger being movable in a second direction that is perpendicular to the first direction between a disengaged position in which the central finger is spaced from the outer fingers in the second direction to an engaged position in which the central finger at least partially aligns with the outer fingers in the second direction; and a controller configured to activate the robotic arm to engage the literature on the tray at the slot by moving the central finger in the second direction to fold the literature around the central finger and to insert the literature into the bag, the high-volume pharmacy configured to operate by:

disposing the literature in the literature receiving area of the tray and across the slot of the tray;

bringing the literature grabbing mechanism at the distal end of the robotic arm to the tray, positioning the central finger of the literature grabbing mechanism directly above the literature, and positioning the two outer fingers of the literature grabbing mechanism directly below the literature; and moving at least one of the central and outer fingers towards at least one of the other fingers in the second direction that is perpendicular to the first direction and at least partially through the slot of the tray to cause the literature to fold around the central finger.

20. The high-volume pharmacy of claim 19, wherein the controller is further configured to:

rotate the literature from a first orientation that the literature has immediately after the fingers engage the literature to a second orientation that is perpendicular to the first orientation prior to inserting the literature into the bag.

\* \* \* \* \*